US012629113B2

(12) United States Patent
Cowles et al.

(10) Patent No.: US 12,629,113 B2
(45) Date of Patent: May 19, 2026

(54) MULTI-SCREEN IMAGING SYSTEM FOR IMPROVED WORKFLOW

(71) Applicant: Hologic, Inc., Marlborough, MA (US)

(72) Inventors: Caroline Cowles, Brookfield, CT (US); Timothy N. Wells, Manchester, CT (US)

(73) Assignee: Hologic, Inc., Marlborough, MA (US)

( * ) Notice: Subject to any disclaimer, the term of this patent is extended or adjusted under 35 U.S.C. 154(b) by 181 days.

(21) Appl. No.: 18/656,906

(22) Filed: May 7, 2024

(65) Prior Publication Data

US 2024/0382165 A1     Nov. 21, 2024

Related U.S. Application Data

(63) Continuation of application No. 17/278,973, filed as application No. PCT/US2019/052721 on Sep. 24, 2019, now Pat. No. 12,011,305.

(60) Provisional application No. 62/735,268, filed on Sep. 24, 2018.

(51) Int. Cl.
    | | |
    |---|---|
    | *A61B 6/04* | (2006.01) |
    | *A61B 6/02* | (2006.01) |
    | *A61B 6/46* | (2024.01) |
    | *A61B 6/50* | (2024.01) |

(52) U.S. Cl.
    CPC ............ *A61B 6/0414* (2013.01); *A61B 6/025* (2013.01); *A61B 6/462* (2013.01); *A61B 6/464* (2013.01); *A61B 6/467* (2013.01); *A61B 6/502* (2013.01); *A61B 2562/0219* (2013.01); *A61B 2562/0257* (2013.01)

(58) Field of Classification Search
    CPC ........ A61B 6/0414; A61B 6/025; A61B 6/462
    See application file for complete search history.

(56) References Cited

U.S. PATENT DOCUMENTS

| | | |
|---|---|---|
| D563,553 S | 3/2008 | Saito |
| D659,832 S | 5/2012 | Ogura |
| D659,833 S | 5/2012 | Ogura |

(Continued)

FOREIGN PATENT DOCUMENTS

| | | |
|---|---|---|
| CN | 302191919 | 11/2012 |
| CN | 307942960 | 3/2023 |

(Continued)

OTHER PUBLICATIONS

Barrosbuenader, Cecilia, Pin on Buying Guide, Nov. 23, 2022, Pinterest, Retrieved from Internet: https://www.pinterest.com/pin/1103733821166578565/, 1 page.

(Continued)

*Primary Examiner* — Hugh Maupin
(74) *Attorney, Agent, or Firm* — Merchant & Gould P.C.

(57) ABSTRACT

A tube arm assembly is rotatably connected to the floor mounted gantry of a breast imaging system. A support arm connected to the tube arm assembly can be independently rotated and positioned in a first angle, second angle, and a level position. A compression arm is configured to support a breast compression paddle and is linearly positionable on the support arm. Display screens and a sensor are disposed on an upper surface of the compression arm. Based on a signal received from the sensor, a controller is configured to change the read-ready orientation of each arm display.

20 Claims, 16 Drawing Sheets

(56) References Cited

U.S. PATENT DOCUMENTS

| | | | |
|---|---|---|---|
| D728,106 S | 4/2015 | Laukkanen | |
| D728,793 S | 5/2015 | Kim | |
| D728,794 S | 5/2015 | Kim | |
| D767,140 S | 9/2016 | Yao | |
| D788,310 S | 5/2017 | Takeuchi | |
| 9,766,788 B2 | 9/2017 | Kerr et al. | |
| D814,636 S | 4/2018 | Bouldier | |
| D865,967 S | 11/2019 | Ten Cate | |
| D892,334 S | 8/2020 | Ye | |
| 11,622,736 B2 | 4/2023 | DeFreitas | |
| D1,032,843 S | 6/2024 | Wells | |
| D1,040,350 S | 8/2024 | Ono | |
| D1,041,010 S | 9/2024 | Ono | |
| D1,050,440 S | 11/2024 | Zhang | |
| D1,054,035 S | 12/2024 | Wells | |
| 2005/0113681 A1 | 5/2005 | DeFreitas | |
| 2008/0095420 A1 | 4/2008 | Ohyu | |
| 2008/0269613 A1 | 10/2008 | Summers | |
| 2009/0016491 A1 | 1/2009 | Li | |
| 2009/0080765 A1* | 3/2009 | Bernard | G06T 11/008 |
| | | | 382/128 |
| 2009/0135996 A1 | 5/2009 | Muller | |
| 2011/0137132 A1* | 6/2011 | Gustafson | A61B 5/4312 |
| | | | 600/300 |
| 2011/0158383 A1 | 6/2011 | Ranjan | |
| 2013/0259193 A1 | 10/2013 | Packard | |
| 2016/0100760 A1 | 4/2016 | Ryu | |
| 2016/0166222 A1 | 6/2016 | Kim | |
| 2016/0206264 A1 | 7/2016 | Fukuda | |
| 2017/0000436 A1 | 1/2017 | Shimada | |
| 2017/0367669 A1 | 12/2017 | Shimada | |
| 2018/0271467 A1 | 9/2018 | Nishi | |
| 2022/0031262 A1 | 2/2022 | Cowles | |
| 2022/0233165 A1 | 7/2022 | Park | |
| 2024/0065660 A1 | 2/2024 | Gemma | |

FOREIGN PATENT DOCUMENTS

| | | |
|---|---|---|
| EM | 2717173 | 6/2015 |
| EM | 002352492-0003 | 2/2016 |
| EM | 001417422-0003 | 8/2016 |
| EM | 009192511 | 10/2022 |
| EM | 015006439-0001 | 9/2023 |
| GB | 6219576 | 7/2022 |
| KR | 3006032090000 | 6/2011 |
| WO | 2018/098321 | 5/2018 |

OTHER PUBLICATIONS

Dubinsky, Lauren, Siemens unveils its MAMMOMAT Revelation mammography system at RSNA, published on: Nov. 26, 2017, Health Care Business News, Retrieved from Internet: https://www.dotmed.com/news/story/40368, 2 pages.

FDA, Mammoscan 510k, published on: Feb. 24, 2022, accessdata.fda.gov, Retrieved from Internet: https://www.accessdata.fda.gov/cdrh_docs/pdf21/K210151.pdf, 2 pages.

Hologic, 3Dimensions Digital Mammography System Part No. MAN-05085-002 Revision 002, User Guide, Dec. 13, 2018, 184 pages.

Hologic: "3Dimensions Digital Mammography System", May 30, 2018, XP055642986, retrieved on Nov. 15, 2019 from the internet at: URL:http://usermanual.wiki/Hologic/PCB01647.User-manual-3-Dimensions-RFID-Updates-EN-part-1/pdf, p. 24-p. 26, figures 1, 2, 6-11 (96 pgs.).

Imaging Technology News, Ashley County Medical Center Installs Arkansas' First Fujifilm Aspire Cristalle With DBT, Published on: Aug. 27, 2019, itnonline.com, Retrieved from Internet: https://www.itnonline.com/content/ashley-county-medical-center-installs-arkansas-first-fujifilm-aspire-cristalle-dbt, 2 pages.

Imaging Technology News, GE Healthcare Announces CE Marking for Its Breast Tomosynthesis Solution, SenoClaire, published on: Jul. 23, 2013, itnonline.com, Retrieved from Internet: https://www.itnonline.com/content/ge-healthcare-announces-ce-marking-its-breast-tomosynthesis-solution-senoclaire, 2 pages.

Kellner, Tomas, Engineered by Women for Women: Colleagues Band Together to Take Fear Out of Breast Screening, Published on: Nov. 26, 2017, ge.com, Retrieved from Internet: https://www.ge.com/news/reports/engineered-women-women-colleagues-band-together-take-fear-breast-screening, 2 pages.

PCT International Preliminary Report on Patentability in International Application PCT/US2019/052721, mailed Apr. 1, 2021, 8 pages.

Applied Radiology, Hologic Showcases Mammography, AI, Breast Biopsy, and Surgical Solutions at RSNA, Pub: Dec. 2024, appliedradiology.com, Retrieved from: https://appliedradiology.com/articles/hologic-showcases-mammography-ai-breast-biopsy-and-surgical-solutions-at-rsna (Year: 2024), 1 page.

* cited by examiner

940

946

944

942

SYSTEM MEMORY

DISPLAY SETTING AND CONTROLS

VOLATILE

NON-VOLATILE

PROCESSING UNIT(S)

REMOVABLE STORAGE — 948

NON-REMOVABLE STORAGE — 951

OUTPUT DEVICES — 956

INPUT DEVICES — 954

COMMUNICATION CONNECTION(S) — 952

MULTI-SCREEN IMAGING SYSTEM FOR IMPROVED WORKFLOW

CROSS REFERENCE TO RELATED APPLICATIONS

This application is a continuation of U.S. patent application Ser. No. 17/278,973, filed Mar. 23, 2021, now U.S. Pat. No. 12,011,305, which is a National Stage Application of PCT/US2019/052721, filed Sep. 24, 2019, which claims the benefit of U.S. Provisional Patent Application No. 62/735,268, filed Sep. 24, 2018, the entire disclosures of which are incorporated herein by reference in their entireties. To the extent appropriate, a claim of priority is made to each of the above disclosed applications.

BACKGROUND

Standard compression methods for mammography and tomosynthesis use a movable, rigid, radiolucent compression paddle. The breast is placed on a breast support platform that typically is flat, and the paddle then compresses the breast, usually while a technologist or other health professional is holding the breast in place. The technologist may also manipulate the breast to ensure proper tissue coverage in the image receptor's field of view. The breast is placed in an imaging area on a breast support platform that typically is flat, and the paddle then compresses the breast, usually while a technologist or other health professional is holding the breast in place. The technologist may also manipulate the breast to ensure proper tissue coverage in the image receptor's field of view. This manipulation and breast placement must also occur while the technologist is actuating various components of the imaging system, which can increase complexity of the procedure. This increased complexity can lead to incorrect placement of the breast or setting of the imaging system components, which can increase the length of time of the procedure and the amount of time that the patient is uncomfortably or incorrectly compressed.

SUMMARY

In one aspect, the technology relates to a breast imaging system having: a floor mount; a gantry supported by the floor mount; a tube arm assembly rotatably connected to the gantry; a support arm independently rotatably connected to the tube arm assembly, wherein the support arm is selectively positionable in a plurality of rotated positions including: a first angled position, a second angled position, and a level position disposed between the first angled position and the second angled position; a compression arm linearly positionable on the support arm, wherein the compression arm is configured to support a breast compression paddle; a plurality of arm display screens disposed on an upper surface of the compression arm; a sensor; and a controller operatively coupled to the sensor and configured to change a read-ready orientation of each of the plurality of arm display screens based at least in part on a signal received from the sensor. In an example, the sensor is configured to detect the rotated position of the support arm. In another example, the sensor is configured to detect an input on a user interface of the breast imaging system. In yet another example, the support arm is in the first angled position: a first arm display screen of the plurality of arm display screens is in a default read-ready orientation, and a second arm display screen of the plurality of arm display screens is in an inverted read-ready orientation. In still another example, when the support arm is in the level position: the first arm display screen of the plurality of arm display screens is in a default read-ready orientation, and the second arm display screen of the plurality of arm display screens is in a default read-ready orientation.

In an example of the above aspect, the support arm is in the second angled position: the first arm display screen of the plurality of arm display screens is in an inverted read-ready orientation, and the second arm display screen of the plurality of arm display screens is in a default read-ready orientation. In an example, the breast imaging system includes a foot display screen disposed on the floor mount, wherein the controller is configured to change a read-ready orientation of the foot display screen based at least in part on the signal received from the sensor. In another example, when the support arm is in the first angled position, the foot display screen is in a first biased read-ready orientation; when the support arm is in the second angled position, the foot display screen is in a second biased read-ready orientation, and when the support arm is in the level position, the foot display screen is in a default read-ready orientation. In yet another example, the foot display screen is configured in a first mode in both the first biased read-ready orientation and the second biased read-ready orientation and in a second mode in the default read-ready orientation. In still another example, the first mode is a portrait mode and the second mode is a landscape mode.

In another example of the above aspect, each of the plurality of arm display screens includes a capacitive touch screen. In an example, the first angled position and the second angled position correspond to mediolateral oblique imaging positions and wherein the level position corresponds to a craniocaudal imaging position. In another example, the plurality of arm display screens include a first arm display screen, a second arm display screen, and a third arm display screen, wherein the first arm display screen and the second arm display screen are configured to display substantially similar information, and wherein the third arm display screen is configured to display information at least partially different than that of the first arm display screen and the second arm display screen. In yet another example, the breast imaging system further includes a gantry interface disposed on the gantry; a support arm interface disposed on the support arm; and a compression arm interface disposed on an upper surface of the compression arm. In still another example, the controller is configured to enable, on at least one of the gantry interface and the compression arm interface, a functionality of the support arm interface when the support arm is disposed in at least one of the first angled position and the second angled position.

In another example of the above aspect, the functionality includes a force application by the compression arm. In an example, the controller is configured to set a presentation of information on at least one of the gantry interface, the support arm interface, and the compression arm interface when a signal from a feedback sensor meets a threshold. In another example, the feedback sensor senses a pressure applied by the compression arm, and wherein the alteration includes changing at least one of a visual data and an audible signal. In yet another example, the compression arm interface includes at least one capacitive touch screen and at least one a tactile button. In still another example, the gantry interface includes a tactile button and wherein the controller is configured to send a signal to a light associated with the tactile button prior to enabling positioning of the support arm.

In another aspect, the technology relates to a method of setting a display orientation of a compression arm display of an imaging system, the method including: sending a default display signal to the compression arm display, wherein the display is disposed on a compression arm of the imaging system; receiving a condition signal from a sensor associated with the imaging system; and if the condition signal meets a first threshold, sending an inverted display signal to the compression arm display. In an example, the imaging system further includes a foot display, and wherein the method further includes: sending a default display signal to the foot display substantially simultaneously with sending the default display signal to the compression arm display; and if the condition signal meets a second threshold, sending an altered display signal to the foot display. In another example, the compression arm display include a plurality of compression arm displays. In yet another example, the inverted display signal is sent to only one of the plurality of compression arm displays. In still another example, sending the altered display signal includes setting: (a) at least one of a portrait display mode and a landscape display mode, and (b) a first-bias mode and a second-bias mode.

In another example of the above aspect, the sensor has at least one of a position sensor, a proximity sensor, and an input sensor. In an example, the input sensor is associated with at least one of a compression arm interface, a support arm interface, and a gantry interface. In another example, the position sensor is configured to detect a position of a support arm. In yet another example, the position sensor has at least one of a gyroscopic sensor and an encoder. In still another example, the method further includes sending a signal to a light associated with a tactile button based at least on the condition signal and a command input.

In another aspect, the technology relates to a breast imaging system including: a gantry supported; a support arm selectively positionable in a plurality of rotated positions relative to the gantry including: a first angled position, a second angled position, and a level position disposed between the first angled position and the second angled position; a compression arm linearly positionable on the support arm; a compression arm display disposed on an upper surface of the compression arm; a sensor; at least one processor; and memory storing instructions that, when executed by the at least one processor, cause the system to perform a set of operations including: sending a default display signal to the compression arm display; receiving a condition signal from the sensor; and if the condition signal meets a first threshold, sending an inverted display signal to the compression arm display.

DETAILED DESCRIPTION

Figure 1A:
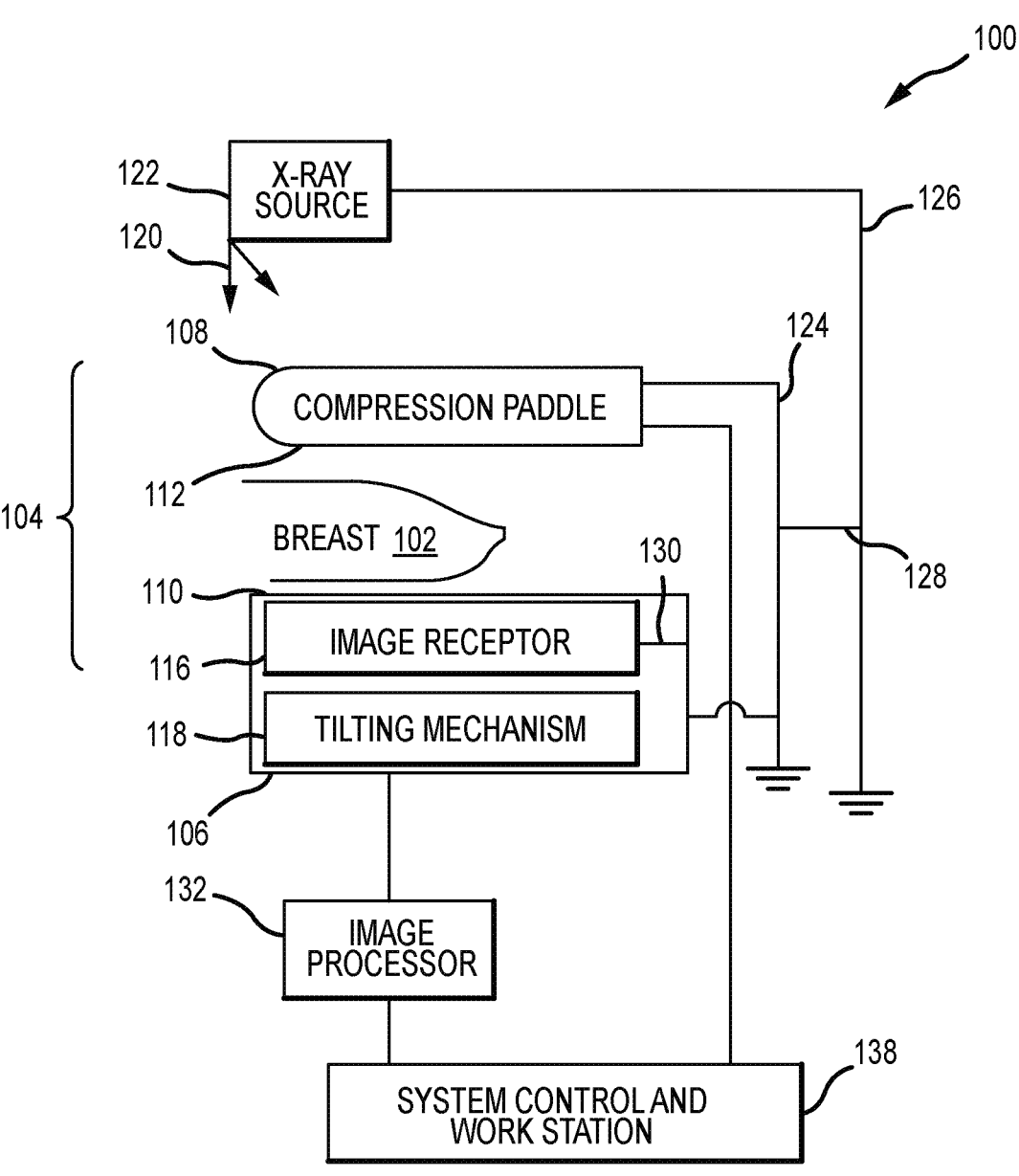
FIG. 1A is a schematic view of an exemplary imaging system.
Figure 1B:
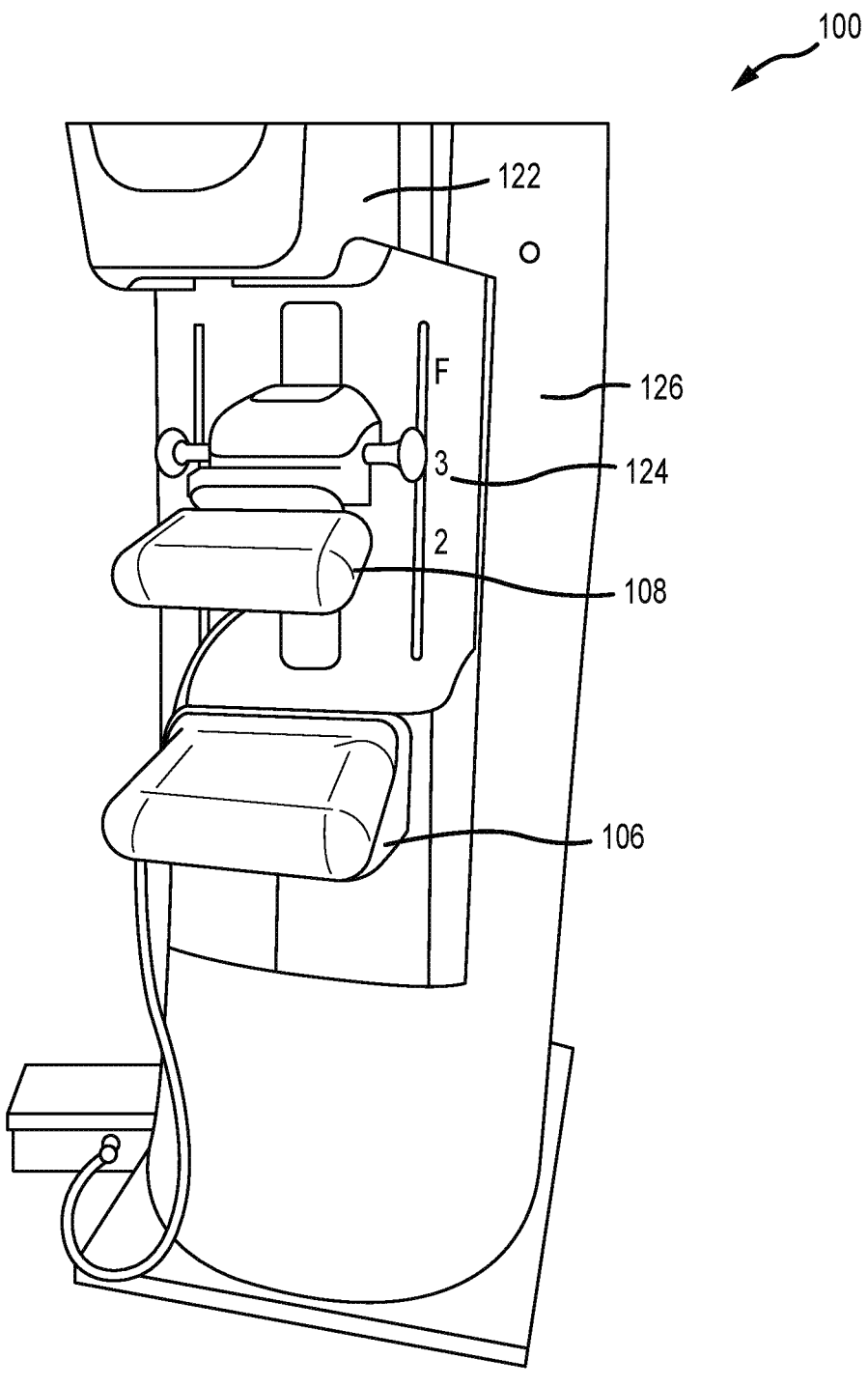
FIG. 1B is a perspective view of the imaging system of FIG. 1A.

FIG. 1A is a schematic view of an exemplary imaging system 100. FIG. 1B is a perspective view of the imaging system 100. Referring concurrently to FIGS. 1A and 1B, the imaging system 100 immobilizes a patient's breast 102 for x-ray imaging (either or both of mammography and tomo-synthesis) via a breast compression immobilizer unit 104 that includes a static breast support platform 106 and a moveable compression paddle 108. The breast support platform 106 and the compression paddle 108 each have a compression surface 110 and 112, respectively, that move towards each other to compress and immobilize the breast 102. In known systems, the compression surface 110, 112 is exposed so as to directly contact the breast 102. The platform 106 also houses an image receptor 116 and, optionally, a tilting mechanism 118, and optionally an anti-scatter grid. The immobilizer unit 104 is in a path of an imaging beam 120 emanating from x-ray source 122, such that the beam 120 impinges on the image receptor 116.

The immobilizer unit 104 is supported on a first support arm 124 and the x-ray source 122 is supported on a second support arm 126. For mammography, support arms 124 and 126 can rotate as a unit about an axis 128 between different imaging orientations such as CC and MLO, so that the system 100 can take a mammogram projection image at each orientation. In operation, the image receptor 116 remains in place relative to the platform 106 while an image is taken. The immobilizer unit 104 releases the breast 102 for movement of arms 124, 126 to a different imaging orientation. For tomosynthesis, the support arm 124 stays in place, with the breast 102 immobilized and remaining in place, while at least the second support arm 126 rotates the x-ray source 122 relative to the immobilizer unit 104 and the compressed breast 102 about the axis 128. The system 100 takes plural tomosynthesis projection images of the breast 102 at respective angles of the beam 120 relative to the breast 102.

Concurrently and optionally, the image receptor 116 may be tilted relative to the breast support platform 106 and in sync with the rotation of the second support arm 126. The tilting can be through the same angle as the rotation of the x-ray source 122, but may also be through a different angle selected such that the beam 120 remains substantially in the same position on the image receptor 116 for each of the plural images. The tilting can be about an axis 130, which can but need not be in the image plane of the image receptor 116. The tilting mechanism 118 that is coupled to the image receptor 116 can drive the image receptor 116 in a tilting motion. For tomosynthesis imaging and/or CT imaging, the breast support platform 106 can be horizontal or can be at an angle to the horizontal, e.g., at an orientation similar to that for conventional MLO imaging in mammography. The system 100 can be solely a mammography system, a CT system, or solely a tomosynthesis system, or a "combo" system that can perform multiple forms of imaging. An example of such a combo system has been offered by the assignee hereof under the trade name Selenia Dimensions.

When the system is operated, the image receptor 116 produces imaging information in response to illumination by the imaging beam 120, and supplies it to an image processor 132 for processing and generating breast x-ray images. A system control and work station unit 138 including software controls the operation of the system and interacts with the operator to receive commands and deliver information including processed-ray images.

One challenge with the imaging system 100 is how to immobilize and compress the breast 102 for the desired or required imaging. A health professional, typically an x-ray technologist, generally adjusts the breast 102 within the immobilizer unit 104 while pulling tissue towards imaging area and moving the compression paddle 108 toward the breast support platform 106 to immobilize the breast 102 and keep it in place, with as much of the breast tissue as practicable being between the compression surfaces 110, 112. This can be a challenge for a technologist who is also operating the various controls of the imaging system 100.

Figure 2A:
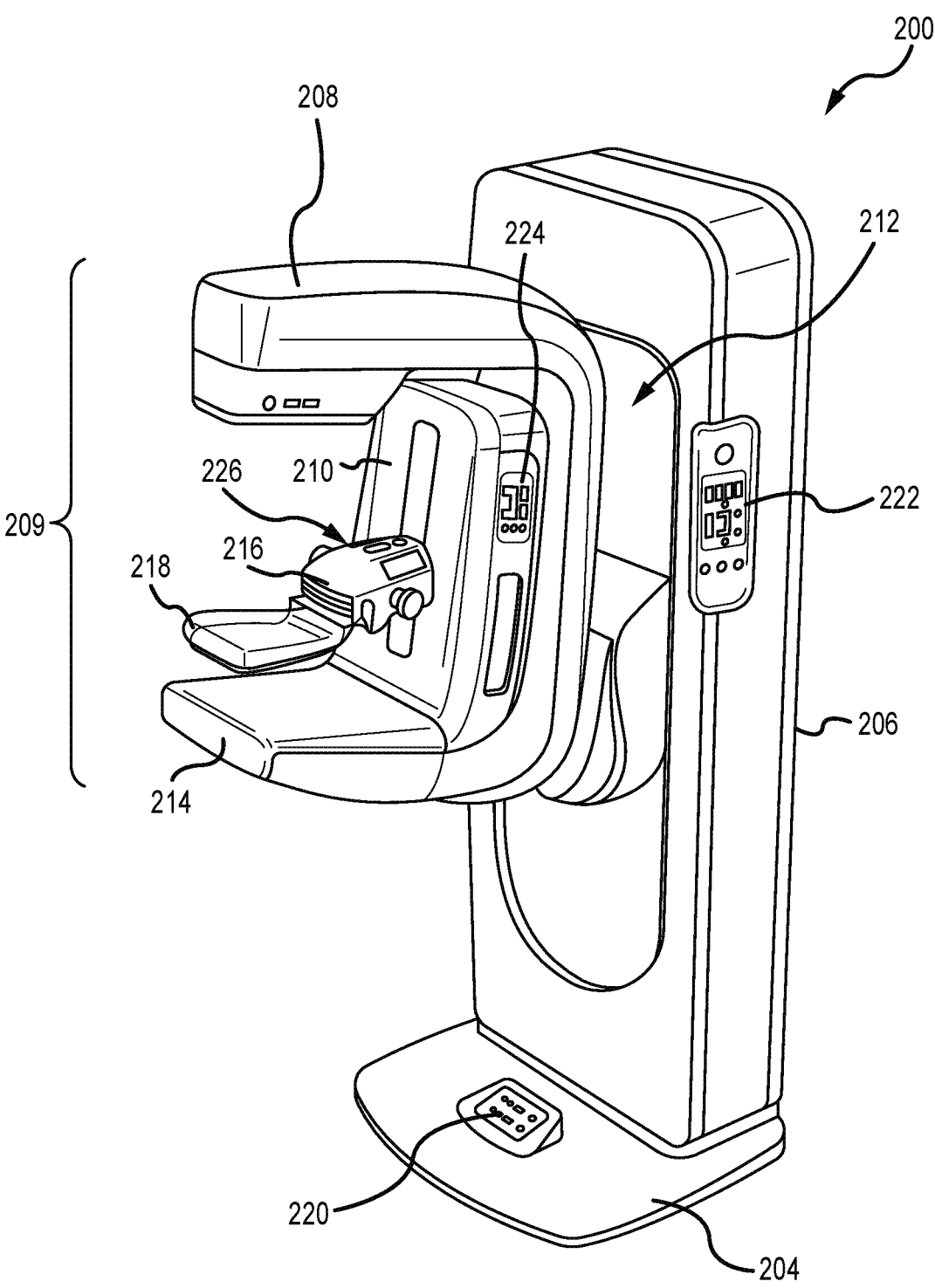
FIGS. 2A-2C depict an exemplary imaging system in various orientations.
Figure 2B:
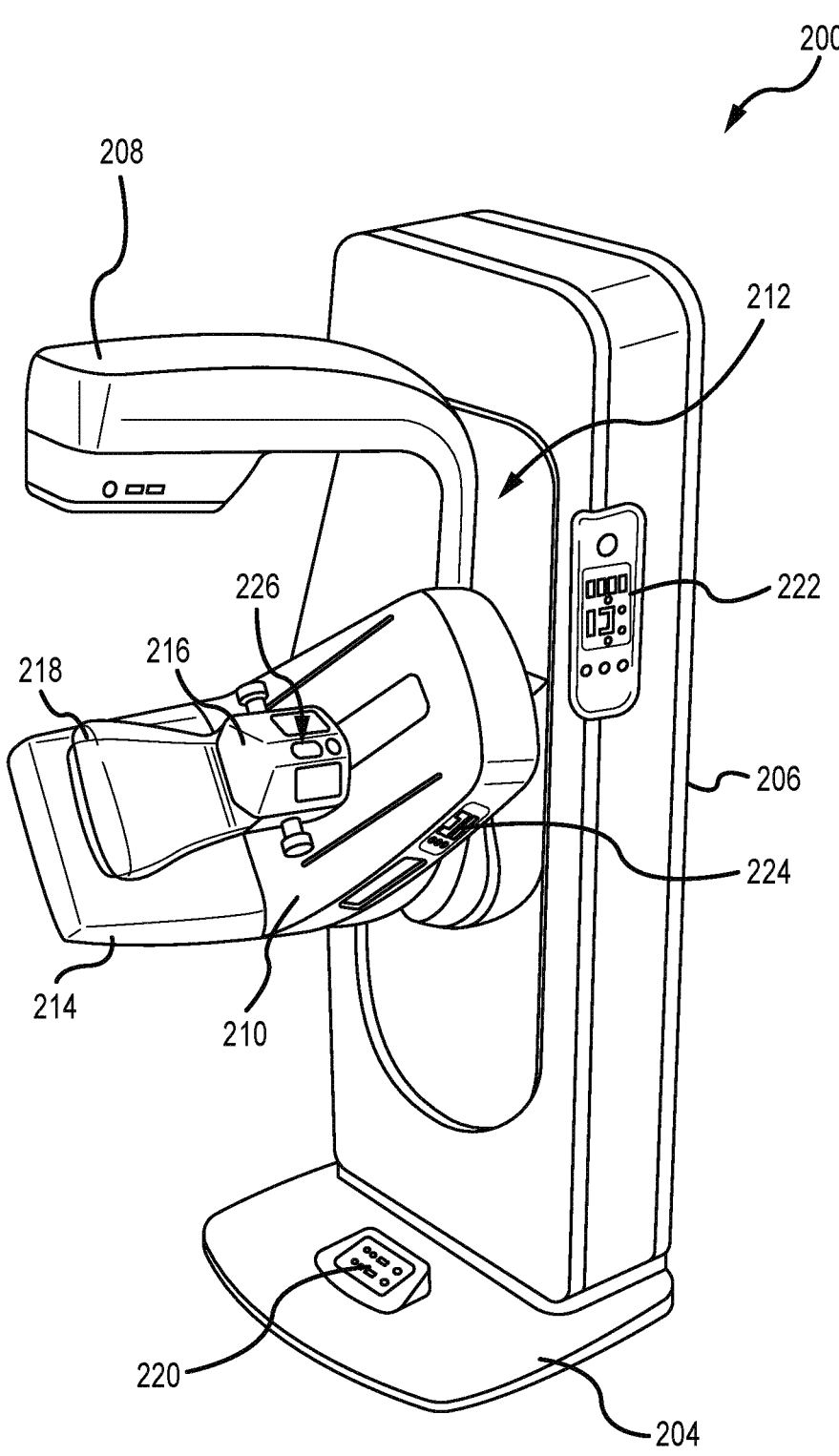
Figure 2C:
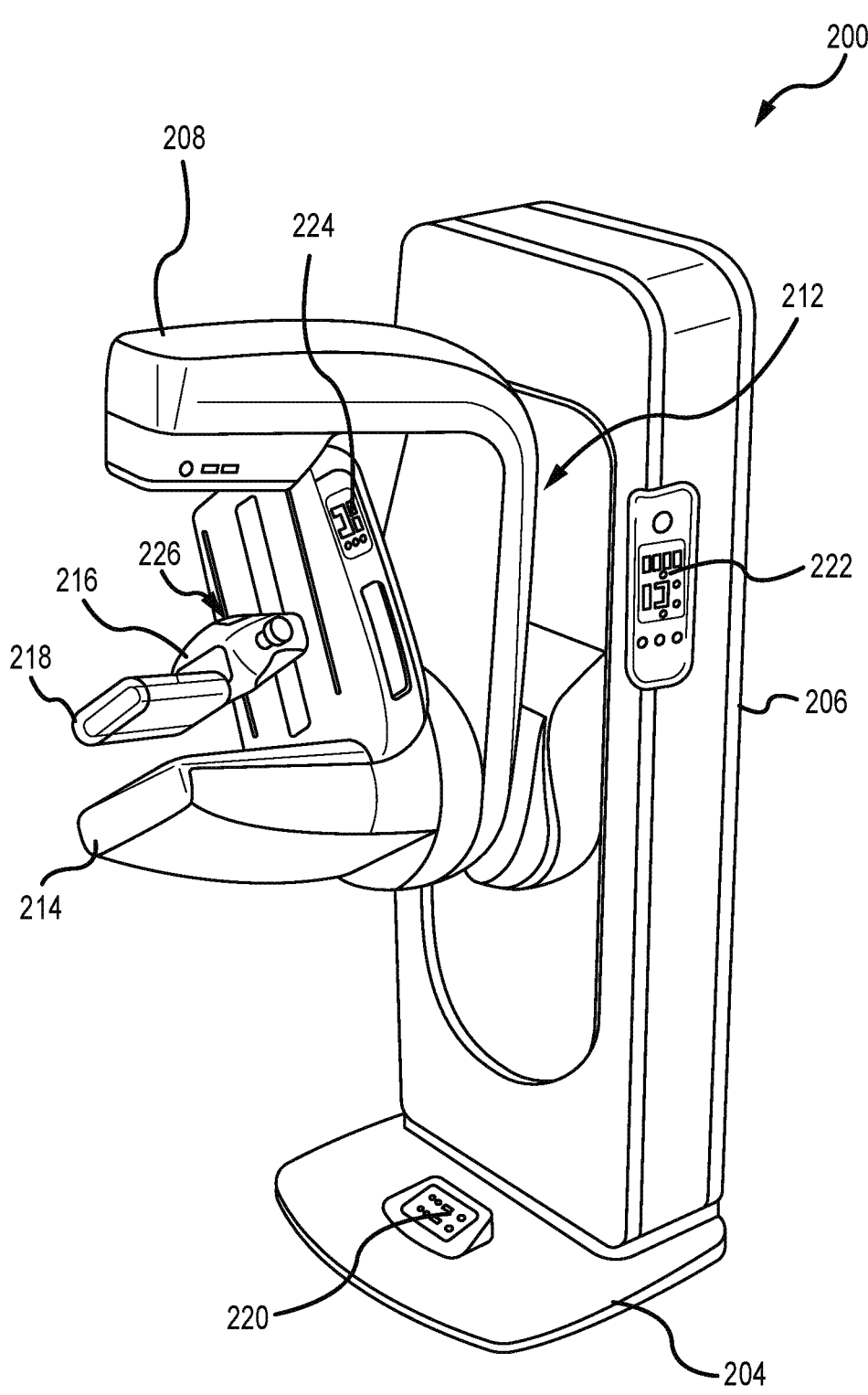

FIGS. 2A-2C depict an exemplary imaging system 200 in various imaging orientations. Specifically, FIG. 2A depicts the imaging system 200 in a craniocaudal (CC) imaging orientation; FIG. 2B depicts the imaging system 200 in a breast positioning state for a right mediolateral oblique (RMLO) imaging orientation; and FIG. 2C depicts the imaging system 200 in a breast positioning state for left mediolateral oblique MLO (LMLO) imaging orientation. In FIGS. 2B and 2C, a tube head 208 of the system 200 is set in an orientation so as to be generally parallel to a gantry 206 of the system 200, or otherwise not normal to the flat portion of a support arm 210 against which the breast is placed. In this position, the technologist may more easily position the breast without having to duck or crouch below the tube head 208. Once the breast is properly positioned, the technologist may press a button on an interface of the system 200 (described below), so as to move the tube head 208 into position to begin an imaging procedure.

The imaging system 200 includes a floor mount or base 202 for supporting the imaging system 200 on a floor. The gantry 206 extends upwards from the floor mount 202 and rotatably supports both the tube head 208 and a support arm 210. The tube head 208 and support arm 210 are configured to rotate discretely from each other and may also be raised and lowered along a face 212 of the gantry so as to accommodate patients of different heights. An x-ray source, described elsewhere herein and not shown here, is disposed within the tube head 208. The support arm 210 includes a support platform 214 that includes therein an x-ray receptor and other components (not shown). A compression arm 216 extends from the support arm 210 and is configured to raise and lower linearly (relative to the support arm 210) a compression paddle 218 for compression of a patient breast during imaging procedures. Together, the tube head 208 and support arm 210 may be referred to as a C-arm 209.

A number of interfaces and display screens are disposed on the imaging system 200. These include a foot display screen 220, a gantry interface 222, a support arm interface 224, and a compression arm interface 226. In general the various interfaces 222, 224, and 226 may include one or more tactile buttons, knobs, switches, as well as one or more display screens, including capacitive touch screens with graphic user interfaces (GUIs) so as to enable user interaction with and control of the imaging system 200. In examples, the interfaces 222, 224, 226 may include control functionality that may also be available on a system control and work station (such as depicted in FIG. 1A). Any individual interface 222, 224, 226 may include functionality available on other interfaces 222, 224, 226, either continually or selectively, based at least in part on predetermined settings, user preferences, or operational requirements. In general, and as described below, the foot display screen 220 is primarily a display screen, though a capacitive touch screen might be utilized if required or desired.

In examples, the gantry interface 222 may enable functionality such as: selection of the imaging orientation, display of patient information, adjustment of the support arm elevation or support arm angles (tilt or rotation), safety features, etc. In examples, the support arm interface 224 may enable functionality such as adjustment of the support arm elevation or support arm angles (tilt or rotation), adjustment of the compression arm elevation, safety features, etc. In examples, the compression arm interface 226 may enable functionality such as adjustment of the compression arm elevation, safety features, etc. Further, one or more displays associated with the compression arm interface 226 may display more detailed information such as compression arm force applied, imaging orientation selected, patient information, support arm elevation or angle settings, etc. The foot display screen 220 may also display information such as displayed by the display(s) of the compression arm interface 226, or additional or different information, as required or desired for a particular application.

In general, the various interfaces and display screens disposed on the imaging system 200 may be used by a technologist during various imaging procedures performed on a patient. The technologies described herein improve efficiency of workflow which may be advantageous for a number of reasons. For example, efficient workflow can reduce the amount of time of an imaging procedure. This helps reduce the stress for the patient and allows the technologist to see a greater number of patients in a given time frame. Technologist performance may also be improved by utilizing the technologies described herein. That is, the technologist may be able to work more comfortably and avoid unnecessary or excessive bending, twisting, or straining during imaging procedures as the technologist works to position the patient and control the imaging system during imaging procedures. This can help reduce repetitive stress to the technologist, as well as reduce fatigue.

Figure 3A:
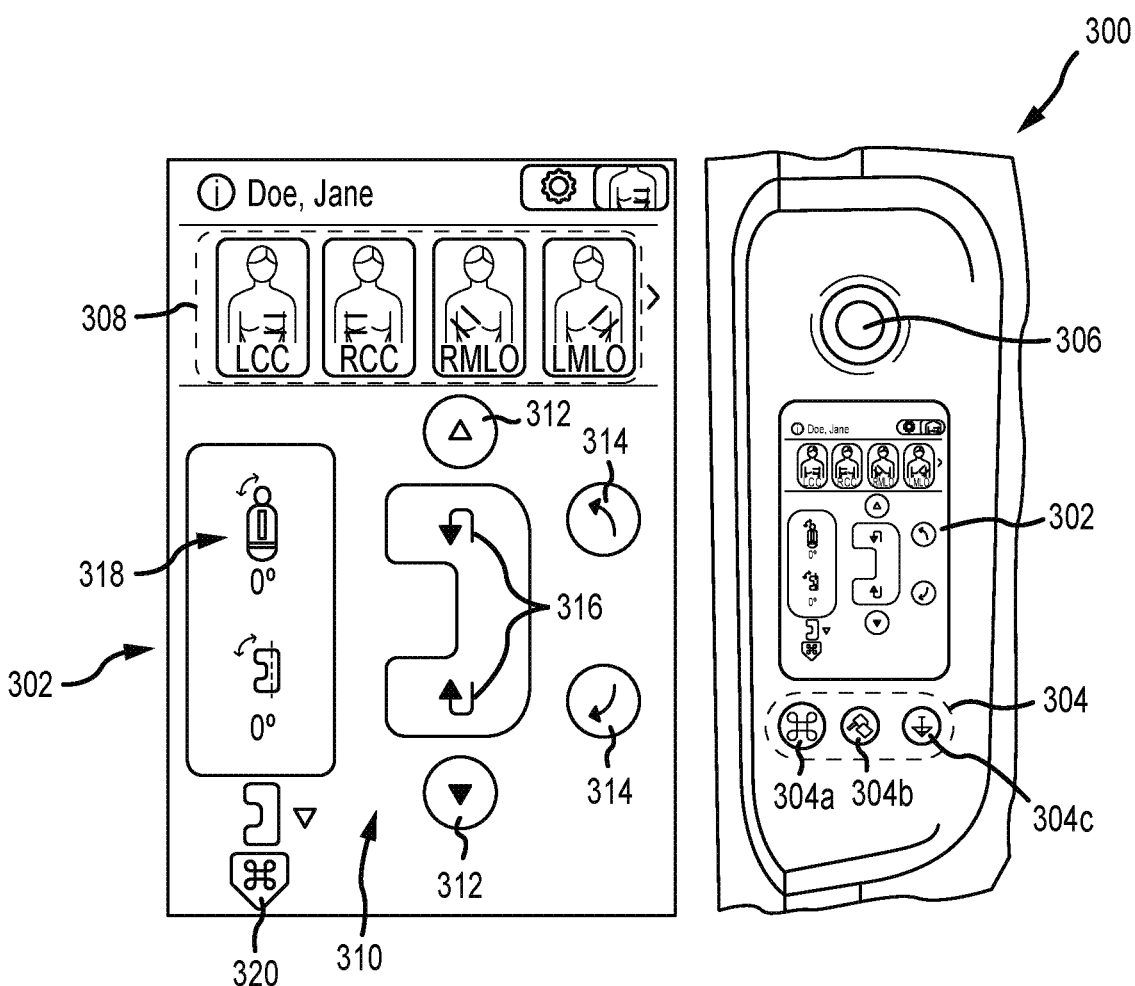
FIGS. 3A-3C depict various views of a gantry interface during imaging procedures.
Figure 3B:
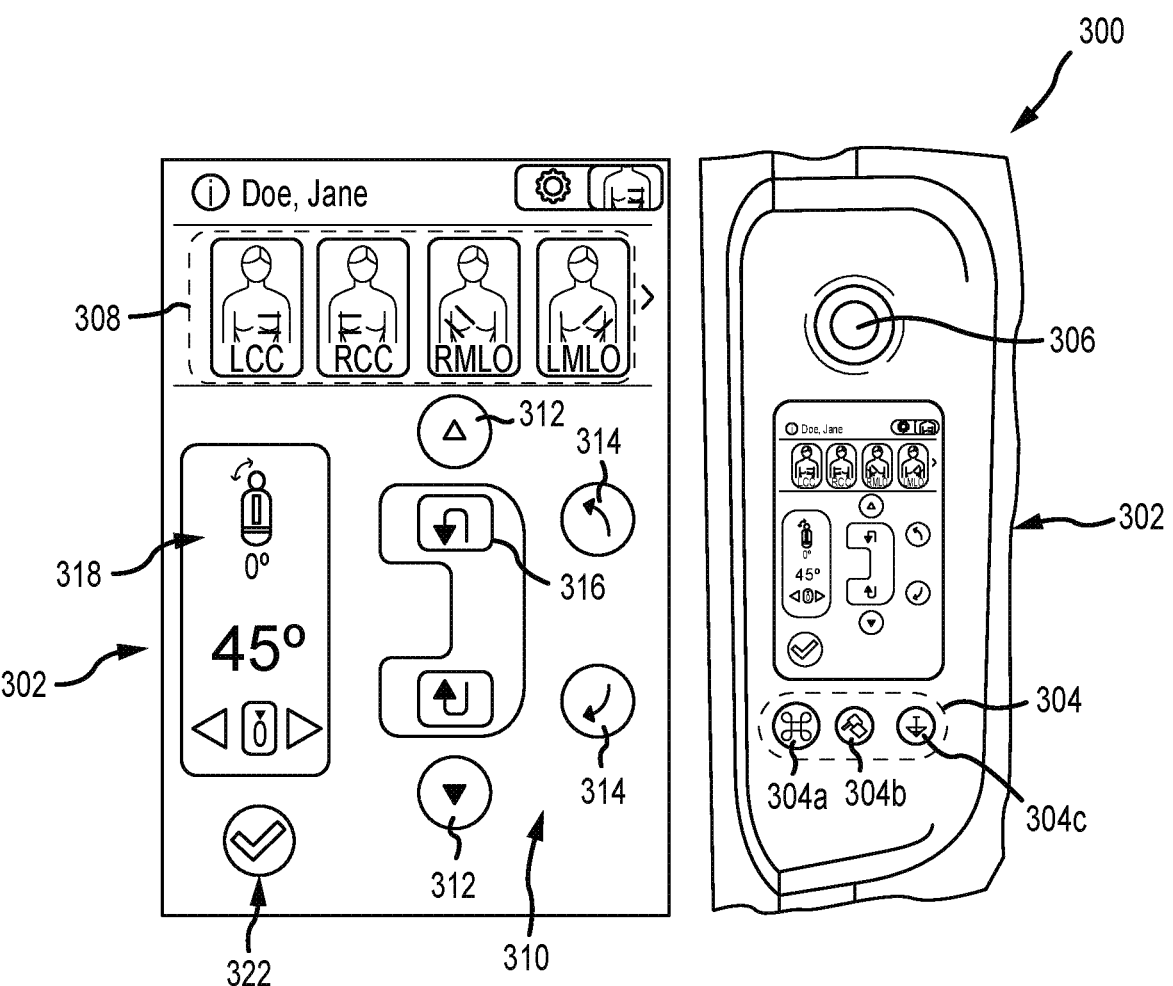
Figure 3C:
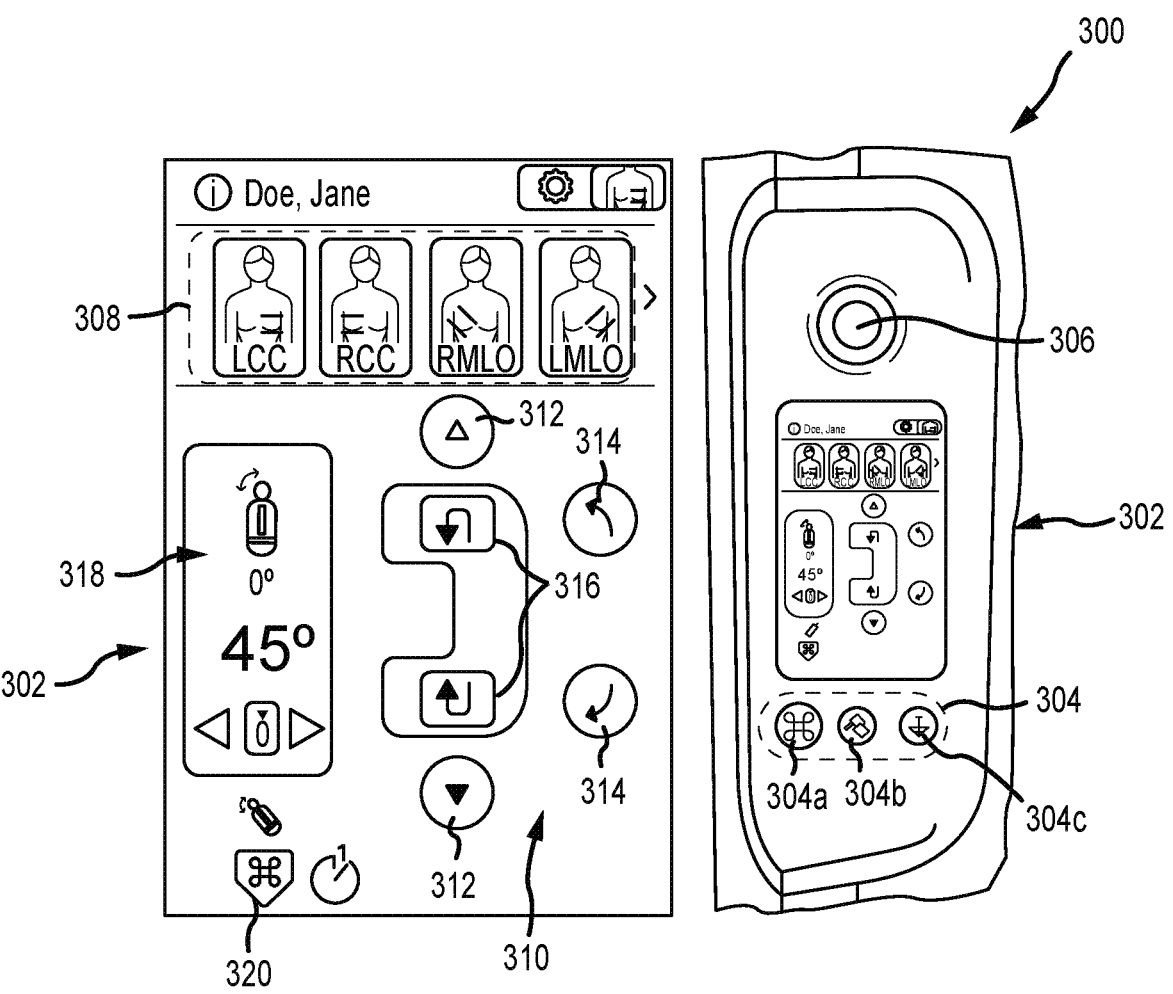

FIGS. 3A-3C depict various views of a gantry interface 300 during imaging procedures and are generally described concurrently. For technologist convenience, a gantry interface is located on both sides of the gantry, so that the technologist will have access to the same controls and information regardless of which side she is working on. Each figure depicts a front view of the gantry interface 300, along with an enlarged view of a graphic user interface (GUI) 302 portion thereof for clarity. In addition to the GUI 302, the gantry interface 300 includes one or more tactile buttons, as well as a tactile SHUTDOWN button 306, which may be used to release the patient from compression in the event of an emergency such as a fire alarm, system failure, power failure, patient panic, etc. The SHUT DOWN button 306 may be connected to a battery-powered electrical circuit, a mechanical release, or a combination thereof to release the patient immediately and/or power the system off. The tactile buttons 304 may be used for any number of functions and may also include a COMMAND button 304*a*, the purpose of which is described below. Additionally, a TUBE HEAD MOVEMENT button 304*b*, which moves the tube head into or out of the way of the technologist is also depicted, as is a COMPRESSION RELEASE button 304*c*. The TUBE HEAD MOVEMENT button 304*b* may be used, e.g., to move the head out of the way of the technologist during positioning of the patient for an RMLO or LMLO imaging procedure (for example, to the position depicted in FIGS. 2B and 2C). The COMPRESSION RELEASE button 304c may be used to release the patient from compression after an imaging procedure. Other or additional buttons having other functionality may be utilized.

The GUI 302 includes a plurality of fields that provide information regarding the patient, the imaging system, and settings thereof. Such patient information may include name, age, medical history, prior x-ray image data, etc. Information regarding the imaging system may include imaging orientation settings, as depicted by an imaging orientation setting field 308, which includes depictions of the imaging orientation for each breast (e.g., left CC (LCC), right CC (RCC), RMLO, LMLO)). These depictions may be highlighted as appropriate or may include a control component where the technologist may select a desired imaging orientation and the system may move to the selected position. The selected position may be associated with preset angles, x-ray doses, or other settings. A C-arm positioning field 310 may include height controls 312 to raise and lower the C-arm, tilt controls 314 to tilt the C-arm towards and away from the gantry, and rotational controls 316 to rotate the C-arm relative to the gantry.

In the depicted configuration of FIG. 3A, tilt and rotational positions are displayed in a C-arm status field 318, although other information, e.g., C-arm height, may also or alternatively be displayed. FIG. 3A also depicts a selectively illuminable COMMAND field 320 that illuminates when C-arm movement is possible (e.g., when the patient breast is not compressed). For example, the technologist may enter desired settings as regards to C-arm tilt, rotation, height, etc. for a particular procedure. Sensors in the compression arm or elsewhere may detect whether a breast of a patient is presently under compression. If so, the illuminable COMMAND field 320 will not light, or may blink as a warning. The technologist must first release compression (e.g., via the COMPRESSION RELEASE button 304c), thus releasing the patient from compression. Once released, the field 320 (or associated COMMAND button 304a) may then illuminate. Once the technologist presses the COMMAND button 304a, the C-arm moves to its next position automatically, while the technologist assists the patient for the next imaging procedure.

FIG. 3B depicts an alternative display condition in the C-arm status field 318. Here, the technologist may selectively enter a desired setting of the C-arm, for example, a desired height, tilt position, or in this case, rotational position. Once the desired condition is set, an accept control 322 is pressed and the selectively illuminable COMMAND field 320 is illuminated (as depicted in FIG. 3C) if the system detects existing breast compression, thus requiring breast release prior to C-arm movement, as described above. The new position of the C-arm may also be depicted in the C-arm status field 318. Although rotation of the C-arm is primarily depicted with regard to FIGS. 3A-3C, similar manipulations for other settings are also contemplated. Further, while the GUI 302 is depicted in FIGS. 3A-3C depicts selectable controls and display fields, the GUI may also display images previously obtained from patients (e.g., historical images), images obtained during the present procedure, or other medical information (e.g., patient physical conditions that may make standing or breast placement difficult). Thus, the gantry interface 300 may display a significant amount of information for the technologist, information that is typically only available at the remote workstation.

Figure 4:
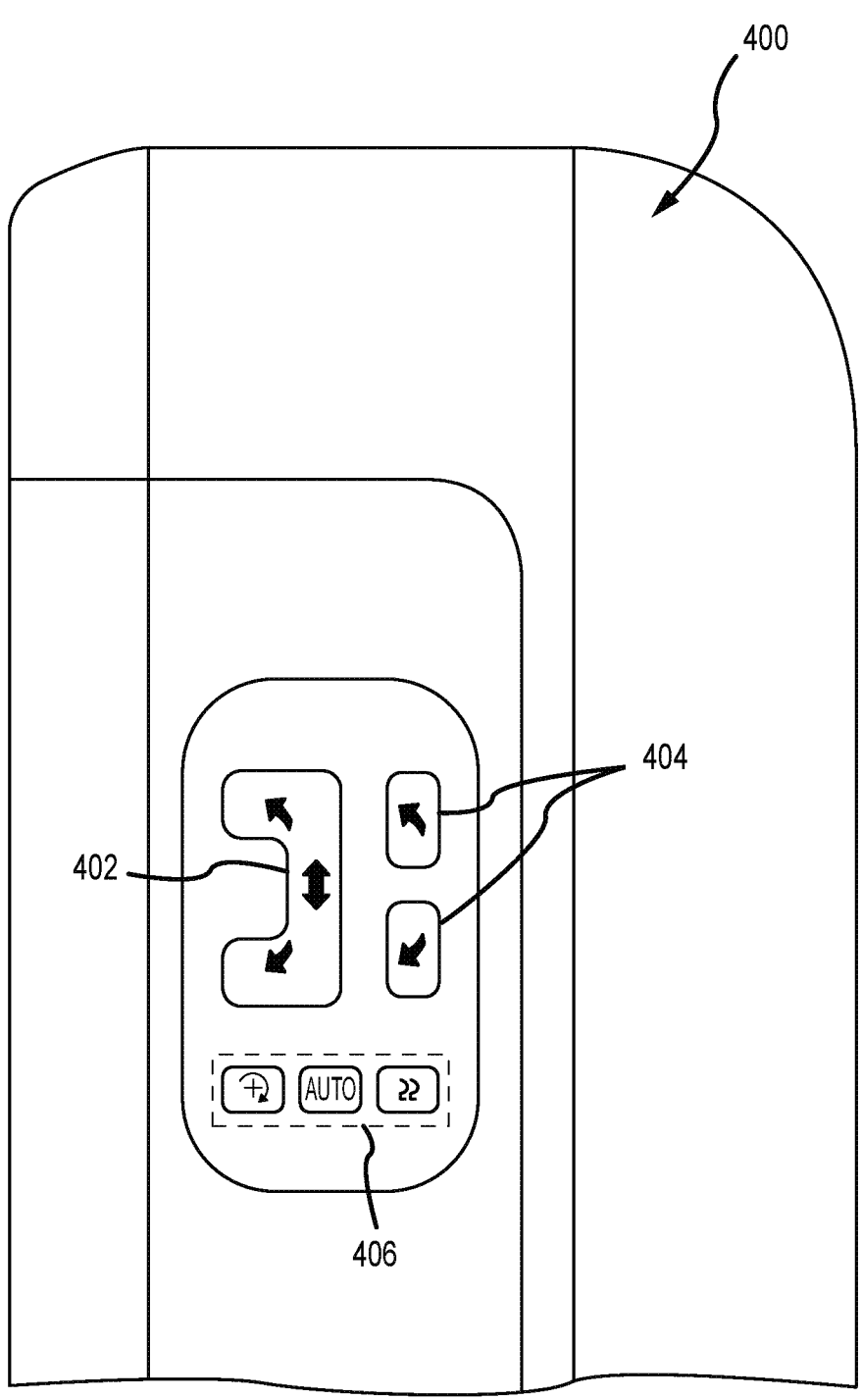
FIG. 4 depicts a support arm interface.

FIG. 4 depicts a support arm interface 400 that includes a plurality of tactile buttons. In general, the support arm interface 400 includes controls utilized to position the C-arm, as well as the compression paddle. For example, the depicted support arm interface includes a C-arm height and rotation button 402, as well as C-arm tilt buttons 404. The C-arm height and rotation button 402 may be a multi-way toggle button that allows for activation of the various controls by pressing various locations on the button 402. In other examples, the C-arm height and rotation button 402 may be a plurality of discrete buttons. The C-arm height and rotation button 402 and the C-arm tilt buttons 404 thus enable functionality somewhat similar to that of the gantry interface depicted above. However, the functionality may be generally limited to that needed to position the C-arm as appropriate for imaging procedures. An additional field of compression arm buttons 406 can include those controls required for raising and lowering the compression paddle, releasing the breast from compression, automatic positioning (e.g., of the C-arm, the compression arm, or both), etc. Although the support arm interface 400 depicts tactile buttons, another example may utilize a capacitive touch screen having a GUI, or any combination of tactile and screen inputs or controls. As with the gantry interface, one support arm interface 400 is disposed on either side of the support arm; an arrangement of the buttons that is arranged in a mirror image on the opposite side of the support arm is contemplated in some examples.

Figure 5:
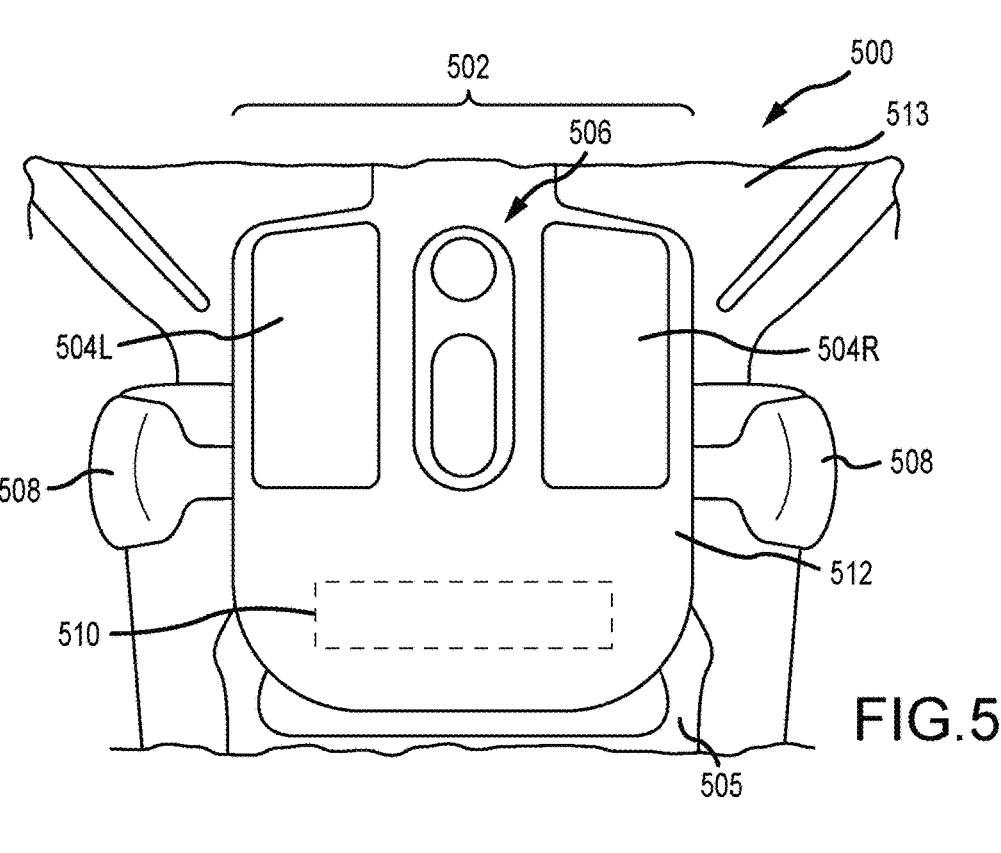
FIG. 5 depicts a top view of a compression arm having a compression arm interface.

FIG. 5 depicts a top view of a compression arm 500 having a compression arm interface 502. The compression arm interface 502 includes a plurality of compression arm display screens 504, which may be simply display screens or capacitive touch screens, for displaying information relevant to the imaging system and, more specifically, the position of the C-arm, elements thereof, and the compression arm 500 and compression paddle 505. A plurality of tactile buttons 506 are also present and may be utilized for increasing or decreasing pressure applied by the compression paddle 505, automatic releasing of the breast from compression, adjusting a distance of the compression arm body 512 from the support arm 513, etc. Further, the compression arm 500 may be manipulated by one or more rotary knobs 508 so as to increase or decrease pressure on the breast. An additional patient display screen 510 may be disposed on a patient-facing portion of the body 512 of the compression arm 500. While the patient display screen 510 may display a limited amount of information, such as patient name and instructions during imaging procedures (e.g., "relax", "hold breath", etc.), the compression arm display screens 504 may display additional information that aids the technologist during positioning of the breast and imaging procedures.

Information displayed on the compression arm display screens 504 typically relates to breast compression and the same information is typically displayed on both the left 504L and right 504R display screens 504. This information may include imaging orientation (e.g., RMLO, LMLO, RCC, LCC), pressure applied to the breast, desired/target/actual breast thickness, C-arm status (rotational and tilt angle), automatic exposure control (AEC) setting, etc. In other examples, system settings initially set by the technologist at other interfaces (e.g., gantry interface or support arm interface) may be displayed on the compression arm display screens 504 so as to improve efficiency of the technologist, eliminating the need for the technologist to return to a different interface while working with the patient proximate the compression arm. In a further benefit, a read-ready orientation of each compression arm display screen 504 may be set automatically by the imaging system to improve readability of each display screen 504 during breast positioning and imaging procedures.

Figure 6A:
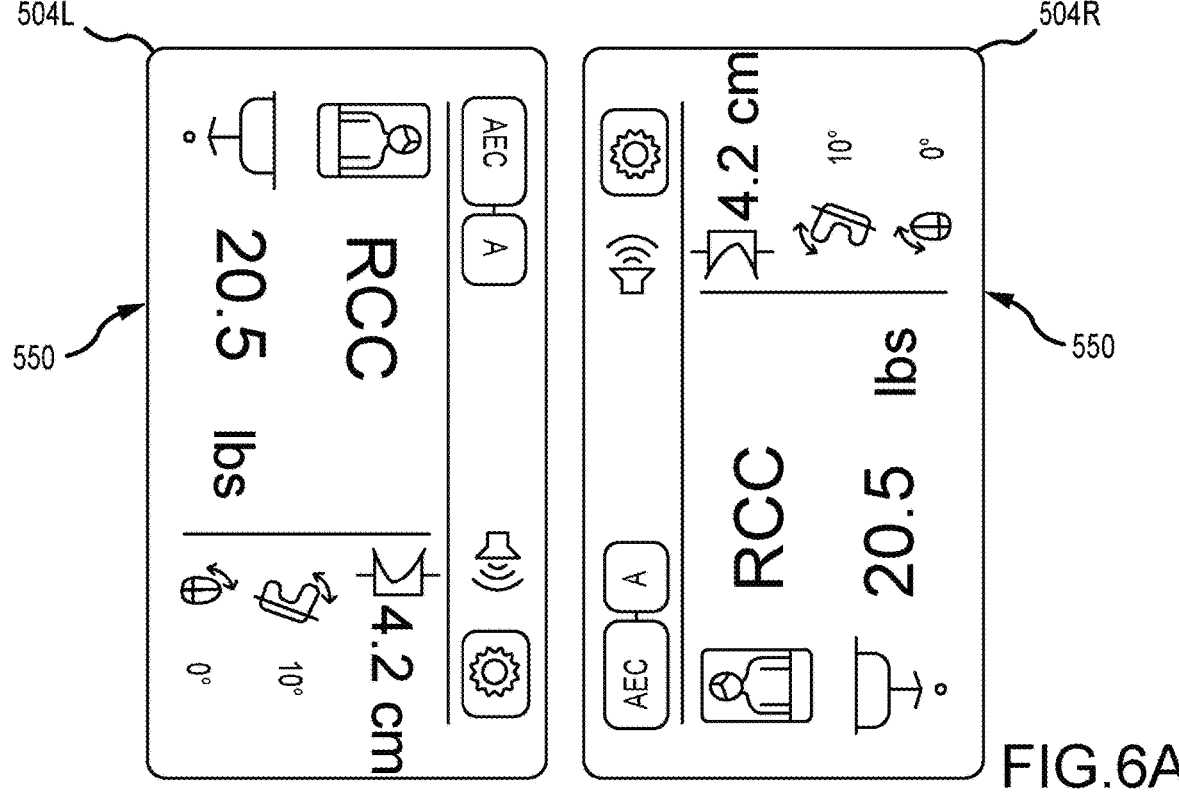
FIGS. 6A-6C depict various views of a compression arm interface during imaging procedures.
Figures 6B, 6C:
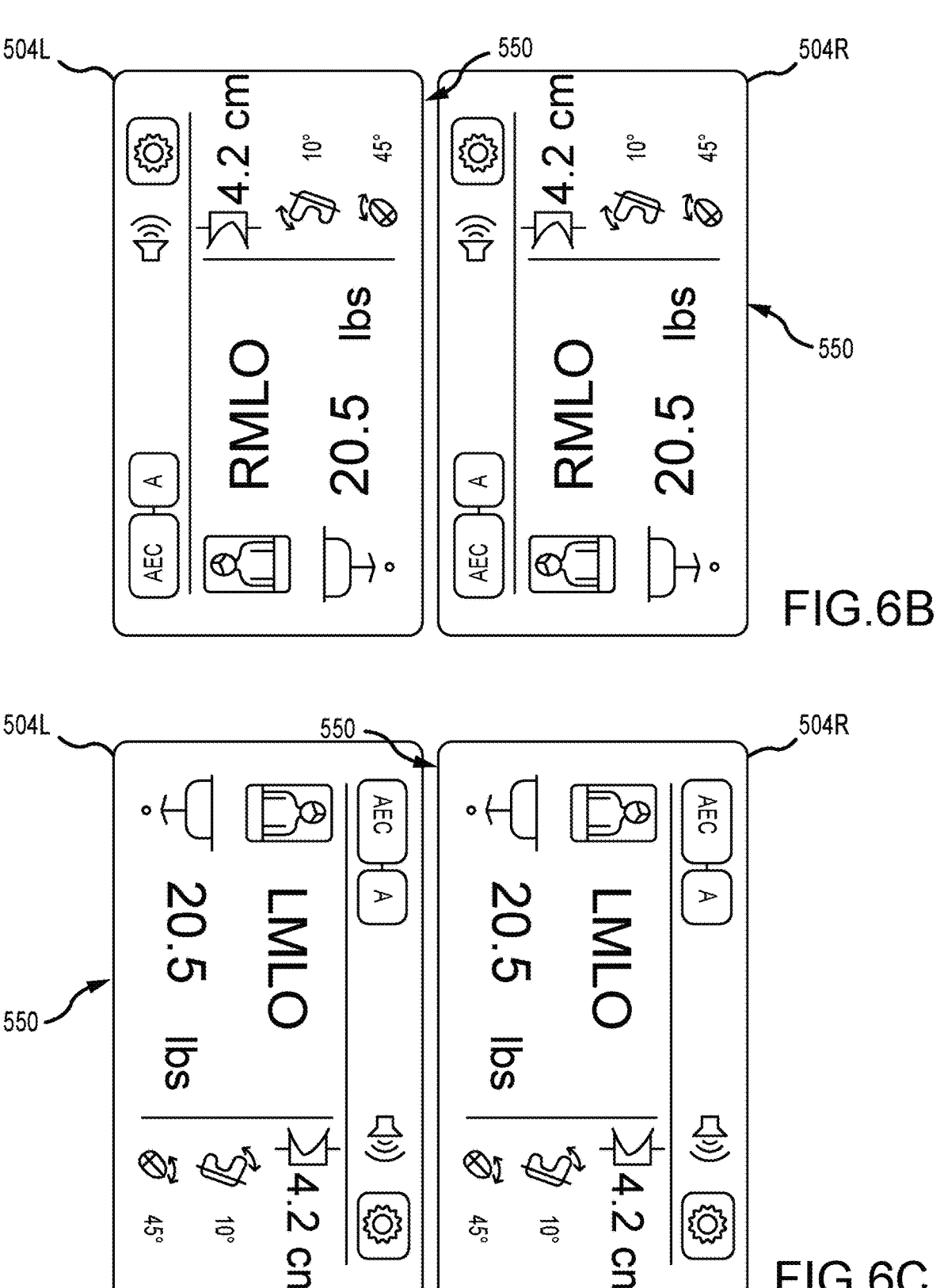

FIGS. 6A-6C depict various views of compression arm interface display screens 504L, 504R during breast positioning and imaging procedures. The read-ready orientation of each of the display screens 504L, 504R may be set so as to change during different stages of the breast positioning procedures. In an example, FIG. 6A depicts the left 504L and right 504R display screens when the imaging system is in a CC (either LCC or RCC) imaging orientation (such as depicted in FIG. 2A). In such a position each display screen is set in a default position. That is, in the default position, a footer edge 550 of each display screen 504L, 504R is positioned so as to be proximate a technologist standing adjacent that particular side of the imaging system. For example, the left display screen 504L has a footer edge 550 facing towards the left of the imaging system, such that a technologist standing on that side may easily read the information on the screen 504L, which appears upright to the technologist. Conversely, the right display screen 504R has a footer edge 550 facing towards the right of the imaging system, such that a technologist standing on that side may easily read the information on the screen 504R, which appears upright to the technologist. Since a technologist may stand on either side of the imaging system during a CC imaging operation, regardless of the technologist's position, the information displayed on the screens 504L, 504R may be easily read. This read-ready orientation of each compression arm display screen 504L, 504R may change as required during other imaging procedures, as described below.

For example, FIG. 6B depicts the display screens 504L, 504R when the imaging system is in the RMLO position. In this position, a number of conditions are present. First, the support arm is rotated to the position depicted in FIG. 2B, while the tube head is rotated to a position to avoid interference with the technologist during breast positioning. Typically also, since the right breast is being prepared for imaging in this position, the technologist will typically be standing on the right side of the imaging system and patient. With the support arm and compression arm positioned as depicted, the right display screen 504R is very difficult to see by a technician of average height unless the technician is crouching. As such, the read-ready orientation of the left display screen 504L changes to an inverted position, where the footer edge 550 is disposed so as to face opposite of its default position (that is, it faces towards the opposite side of the imaging system from where it is disposed). That is, the footer edge of the left display screen 504L is oriented towards the right of the compression arm and imaging system. The footer edge 550 of the right display screen 504R remains in the default position. In this orientation, a technologist standing on the right side of the imaging system and patient is able to read the left display screen 504L, which is more clearly facing in the direction of the technologist.

Similarly, FIG. 6C depicts the display screens 504L, 504R when the imaging system is in the LMLO position. In this position, a number of conditions are present. First, the support arm is rotated to the position depicted in FIG. 2C, while the tube head is rotated to a position to avoid interference with the technologist during breast positioning. Typically also, since the left breast is being prepared for imaging in this position, the technologist will typically be standing on the left side of the imaging system and patient. With the support arm and compression arm positioned as depicted, the left display screen 504L is very difficult to see by a technician of average height unless the technician is crouching. As such, the read-ready orientation of the right display screen 504R changes to an inverted position, where the footer edge 550 is disposed so as to face opposite of its default position (that is, it faces towards the opposite side of the imaging system from where it is disposed). That is, the footer edge of the right display screen 504R is oriented towards the left of the compression arm and imaging system. The footer edge 550 of the left display screen 504L remains in the default position. In this orientation, a technologist standing on the left side of the imaging system and patient is able to read the right display screen 504R, which is more clearly facing in the direction of the technologist.

Figure 7A:
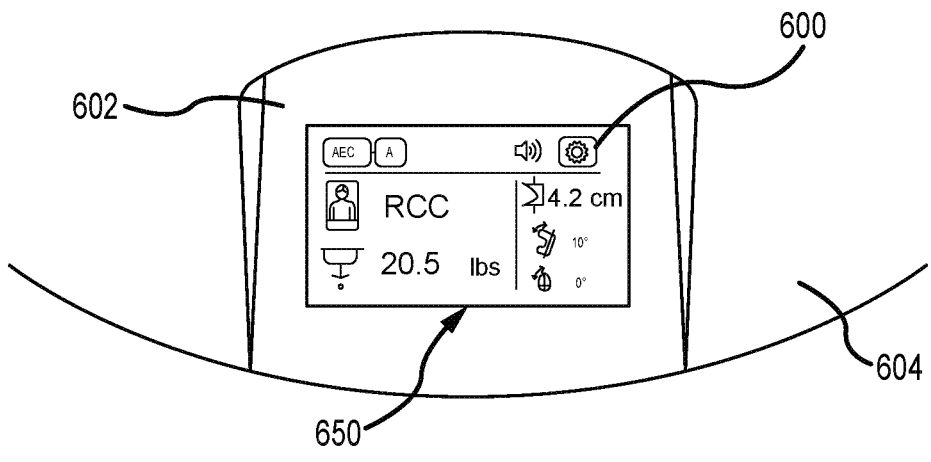
FIGS. 7A-7C depict various views of a foot display screen during imaging procedures.
Figure 7B:
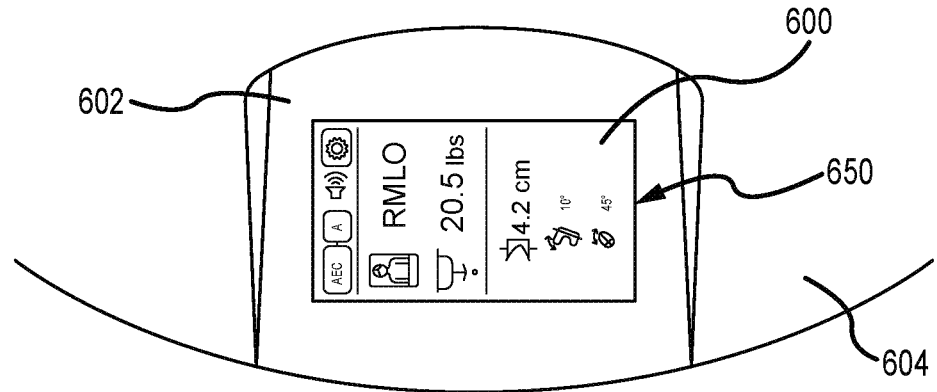
Figure 7C:
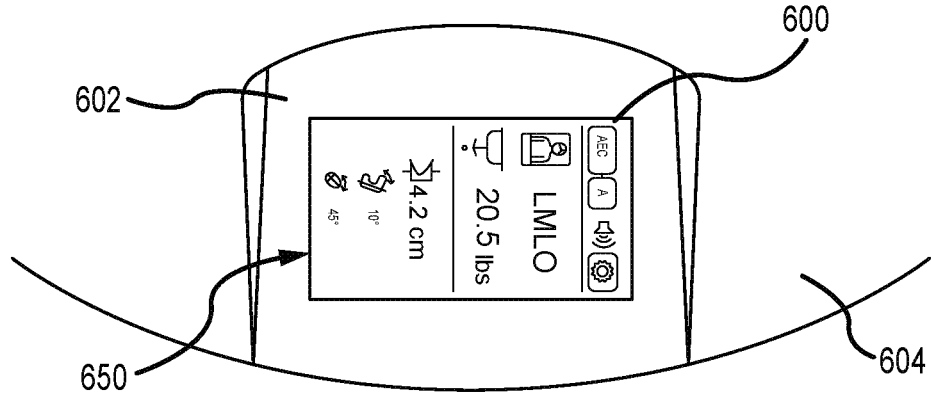

FIGS. 7A-7C depict various views of a foot display screen 600 during imaging procedures. Like the compression arm display screens 504, the read-ready orientation of the foot display screens 600 may be set so as to change during different stages of the breast positioning and imaging procedures. As an initial matter, the foot display screen 600 may be disposed on a ramp 602 that is disposed at an angle to the foot mount 604. An angle of the ramp 602 may improve a technologist's ability to view the foot display screen 600 in any position. The foot display screen 600 may display information similar to that displayed by the compression arm display screens 504 or other information as required or desired.

In an example, FIG. 7A depicts the foot display screen 600 when the imaging system is in a CC (either LCC or RCC) imaging orientation (such as depicted in FIG. 2A). In such a position, the display of the foot display screen is set in a default, landscape position. The term "landscape" has the meaning typically understood by a person of skill in the art. In the default position a footer edge 550 of the foot display screen 504L, 504R is positioned so as to face the patient. Since a technologist may stand on either side of the imaging system during a CC imaging operation, regardless of the technologist's position, the information displayed on the foot display screen 600 may be easily read. This read-ready orientation of the foot display screen 600 may change as required during other imaging procedures.

For example, FIG. 7B depicts the foot display screen 600 when the imaging system is in the RMLO position. In this position, a number of conditions are present. First, the support arm is rotated to the position depicted in FIG. 2B, while the tube head is rotated to a position to avoid interference with the technologist during breast positioning. Typically also, since the right breast is being prepared for imaging in this position, the technologist will typically be standing on the right side of the imaging system and patient. As such, the read-ready orientation of the foot display screen 600 changes to right-biased portrait orientation, where the footer edge 650 is disposed so as to face towards the right side of the imaging system. The term "portrait" has the meaning typically understood by a person of skill in the art. In this orientation, a technologist standing on the right side of the imaging system and patient is able to read the foot display screen 600, if the compression arm displays 504 are not easily viewable.

Similarly, FIG. 7C depicts the foot display screen 600 when the imaging system is in the LMLO position. In this position, a number of conditions are present. First, the support arm is rotated to the position depicted in FIG. 2C, while the tube head is rotated to a position to avoid interference with the technologist during breast positioning. Typically also, since the left breast is being prepared for imaging in this position, the technologist will typically be standing on the left side of the imaging system and patient. As such, the read-ready orientation of the foot display screen 600 changes to left-biased portrait orientation, where the footer edge 650 is disposed so as to face towards the left side of the imaging system. In this orientation, a technologist standing on the left side of the imaging system and patient is able to read the foot display screen 600, if the compression arm displays 504 are not easily viewable.

The various GUIs and display screens described herein (e.g., on the gantry interface, compression arm interface, foot display screen, or other interfaces) may also alter the presentation of information based on predetermined conditions. For example, for screens that display compression force information, the data associated therewith may change in presentation (e.g., color, strobe effect, font size, etc.) as a threshold is approached or exceeded. This threshold could be associated with a previously-identified threshold that typically or previously caused a patient discomfort, or some other threshold or criteria. Additionally, the GUIs and display screens may display instructions for performing particular imaging procedures, which may be helpful for training purposes. Further, the GUIs and display screens may display menus from which various actions may be selected. Other presentations of information are contemplated.

Figure 8:
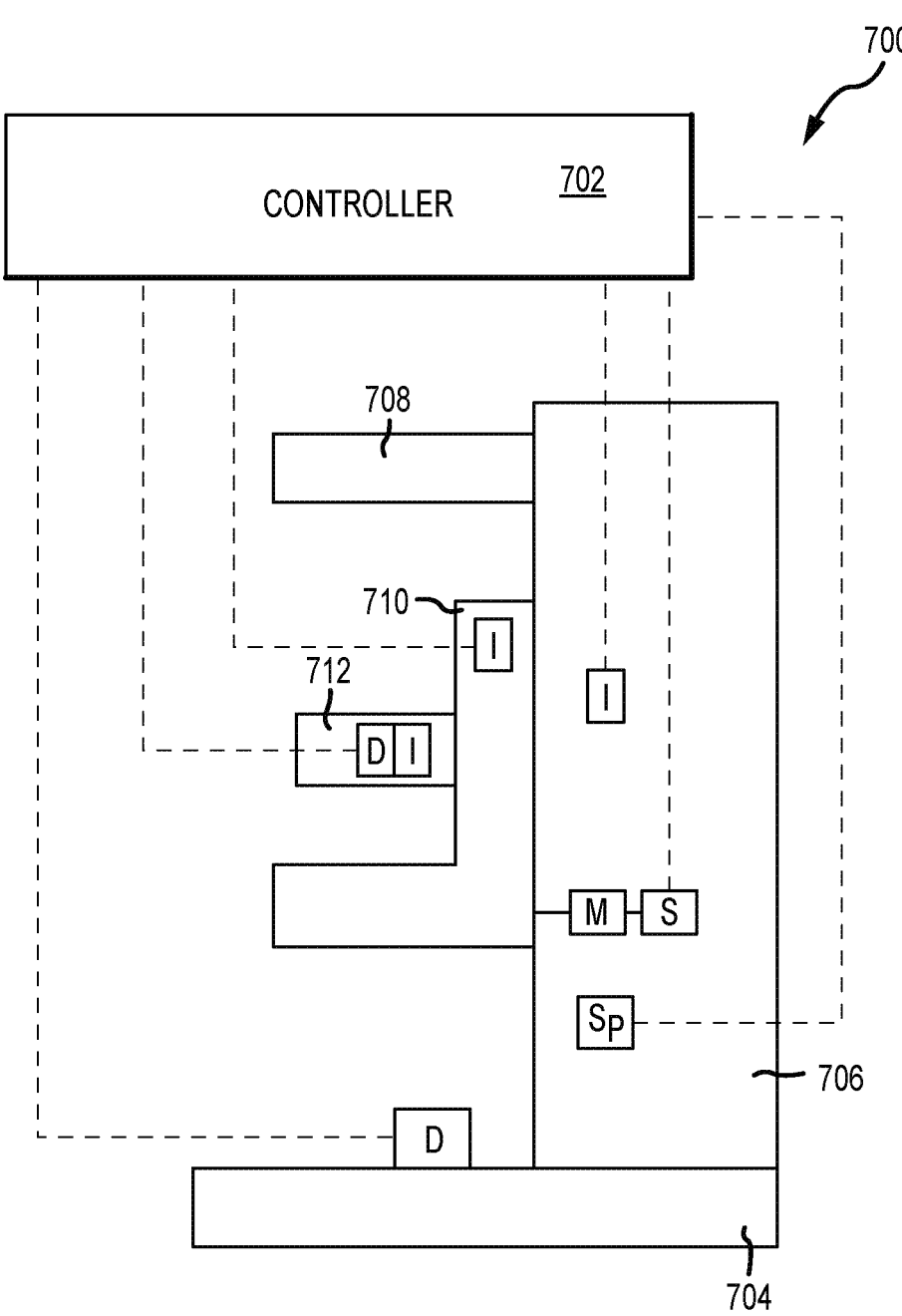
FIG. 8 depicts a schematic diagram of an imaging system.

FIG. 8 depicts a schematic diagram of an imaging system 700. The imaging system 700 may be self-contained, but often includes an associated controller 702, which may be a remote computer or custom workstation that may be connected to a hospital network or just to the imaging system 700 itself. In another example, the controller 702 may be contained within the imaging system 700 itself (e.g., in a gantry 706). The imaging system 700 includes a foot mount or base 704, the gantry 706, a tube head 708, a support arm 710, and a compression arm 712. A number of interfaces I, motors M, sensors S, and displays D are depicted. The imaging systems described herein utilize one or more sensors S to determine the display settings of the foot display D and the displays D associated with the interface I of the compression arm 712. Again, a plurality compression arm displays D are utilized, but only a single display D is shown in FIG. 8 for clarity. In an example, the sensors utilized may be a sensor that is associated with the motor M that is used to rotate the support arm 710 relative to the gantry 706. In another example, the sensors utilized may be a position sensor connected directly to a feature of the support arm 710 itself. In another example, a gyroscopic sensor disposed on the support arm 710 may be utilized. In general, the signal sent from the motor, position, gyroscopic (or other) sensors detect positional relationships of one component of the system 700 to another component. Based on those signals, the controller 702 may send signals that set the read-ready orientations of the various displays D on the compression arm 712 or the display D on the foot 704.

In another example, the sensors need not be positional sensors such as described above, but may be associated with one or more of the interfaces I. For example, command or other signals (e.g., indicative of a GUI selection, button press, knob adjustment, etc.) received from an interface I located on a left side of the imaging system 700 (e.g., the left interface(s) on the gantry 706, support arm 710, or compression arm 712), are generally indicative of a technologist working on that side. As a result, the controller 702 may set the read-ready orientations of the various displays D on the compression arm 712 or the display D on the foot 704 so as to be read from the left side. Of course, signals received from such interface sensors may be ignored if the imaging system 700 is in the CC imaging position, for reasons described above.

In yet another example, one or more proximity sensors Sp may be disposed at various locations around the imaging system 700 (e.g., on either side of the base 704, gantry 706, etc.). These sensors Sp may be motion, heat, or other types of sensors that detect the presence of a person (e.g., the technologist) on one side of the imaging system 700. A signal associated therewith may be sent to the controller 702, to that the controller 702 may set the read-ready orientations of the various displays D on the compression arm 712 or the display D on the foot 704 so as to be read from the appropriate side.

Figure 9:
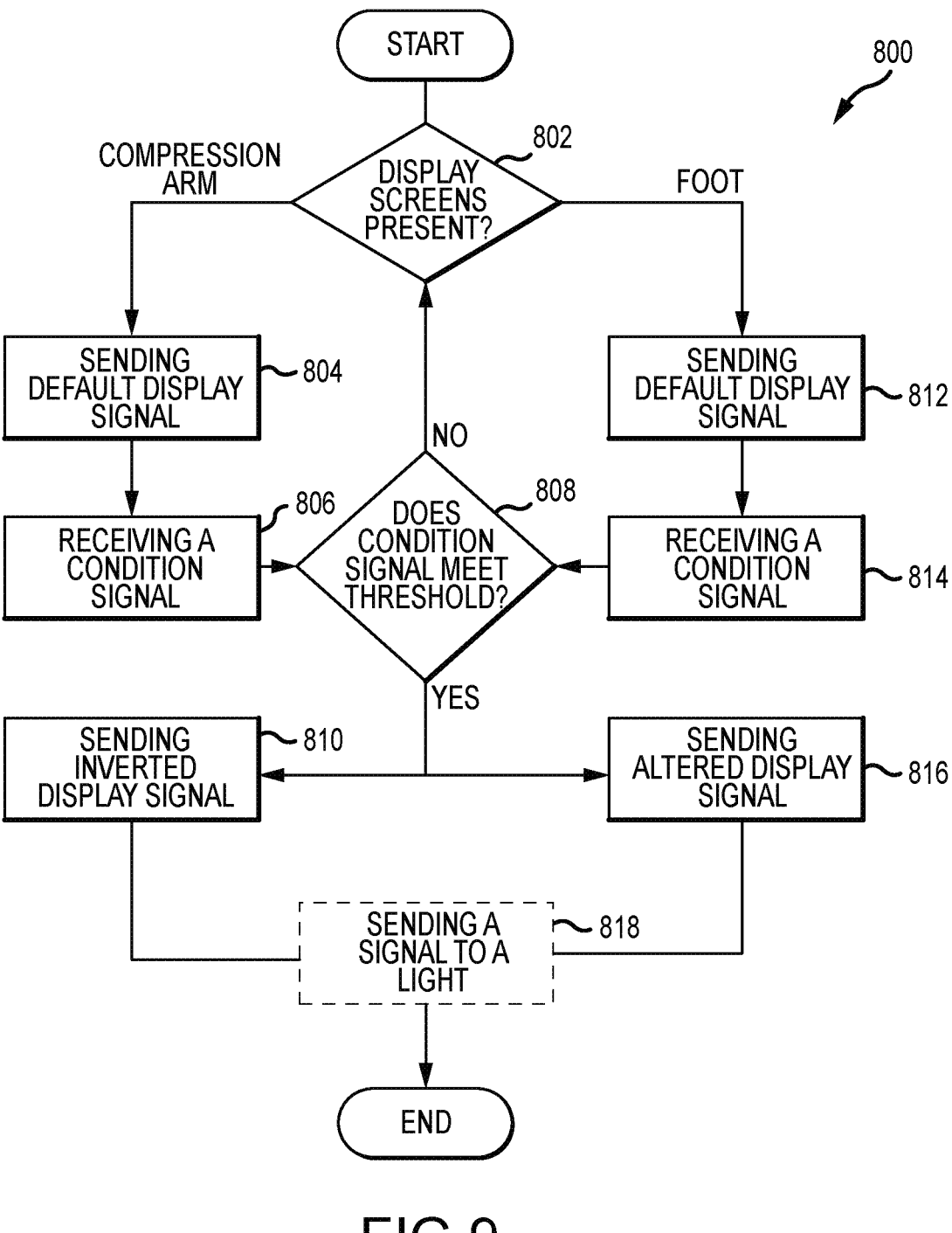
FIG. 9 depicts a method of setting a display orientation for a display in an imaging system.

FIG. 9 depicts a method 800 of setting a display orientation for a display in an imaging system. The method 800 may be performed on imaging systems such as those described herein (e.g., those with multiple display screens and interfaces in various locations thereon). The method 800 includes an identification of the types of displays present, operation 802. As described above, multiple displays may be utilized, such as compression arm display screens and foot display screens. Regarding the method 800 when a compression arm display screen is present in the imaging system, the method begins with sending a default display signal to the compression arm display screen, operation 804. As described above, multiple compression arm display screens may be utilized. In that case, the method 800 may be performed for each compression arm display screen. In general, this default display signal will set the read-ready orientation to a default setting, where the compression arm display screen may be oriented so as to be easily readable by a technologist standing on the side of the imaging system where the compression arm display screen is located. The method continues with receiving a condition signal, operation 806. The condition signal may be received from a sensor such as described above or may be a command or other signal sent from, for example, an interface on a particular component and/or side of the imaging system. In an example, the sensor detects a position of the support arm and may be an encoder, a gyroscope, or some other type of sensor. In operation 808 the condition signal is compared to a threshold and, if it meets that threshold, flow branches YES and the method sends an inverted display signal to the compression arm display screen, operation 810. In examples where a plurality of display screens are present, this signal may only be sent to a single one of the plurality of screens Regarding the method 800 when a foot display screen is present in the imaging system, the method begins with sending a default display signal to the foot display screen, operation 812. This may occur substantially simultaneously with operation 804. In general, this default display signal will set the read-ready orientation to a default setting, where the foot display screen may be oriented so as to be easily readable by a technologist standing on either side of the imaging system. The method continues with receiving a condition signal, operation 814. The condition signal may be received from a sensor such as described above or may be a command or other signal sent from, for example, an interface on a particular component and/or side of the imaging system. In an example, the sensor detects a position of the support arm and may be an encoder, a gyroscope, or some other type of sensor. The method returns to operation 808, where the condition signal is compared to a threshold and, if it meets that threshold, flow branches YES and the method 800 sends an altered display signal to the compression arm display screen, operation 810. In this case, the threshold for comparison regarding the foot display screen may be different than that for the compression arm display screen. That is, the read-ready orientation of the foot display screen may be set when the compression arm reaches a first angle, while the read-ready orientation of the compression arm display screen may be set when the compression arm reaches a second angle. This may allow the foot display screen, for example, to be set to a different read-ready orientation at prior to the compression arm display screen, again for the benefit of the technologist. Sending the altered display signal may include setting the foot display screen to either a portrait or landscape mode, as well as a bias mode to either the left or the right of the imaging device, depending on the signal and the threshold. Optional operation 818 may send a signal to a light associated with a tactile button based on the condition signal and/or a command input. This aspect of the method helps signal the technologist to take a further action (e.g., releasing of the patient from compression) prior to enabling movement of the support arm.

Figure 10A:
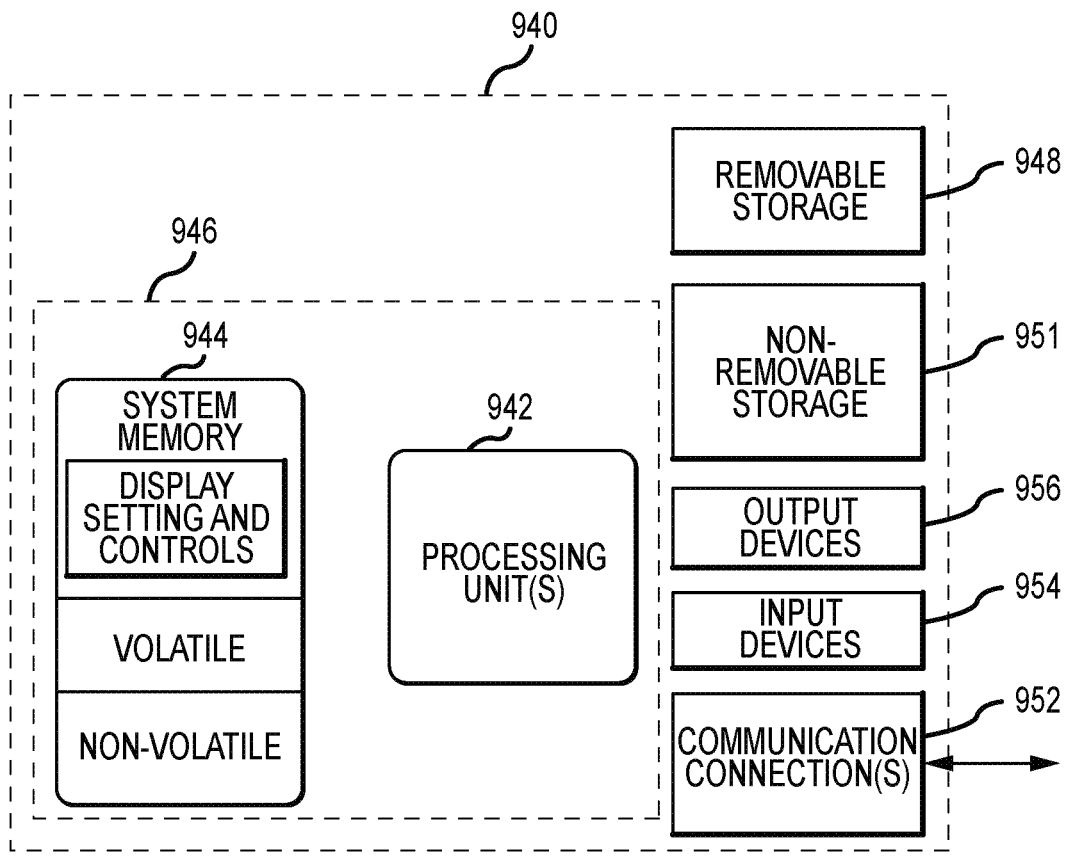
FIG. 10A depicts an example of a suitable operating environment for use with the present examples.

FIG. 10A depicts an example of a suitable operating environment 940 for use with the present examples. The computing device 940 is a suitable operating environment in which one or more of the present examples can be implemented. This operating environment may be incorporated directly into a imaging system, a workstation, or may be incorporated into a computer system discrete from, but used to control or process data from, the imaging systems described herein. This is only one example of a suitable operating environment and is not intended to suggest any limitation as to the scope of use or functionality. Other well-known computing systems, environments, and/or configurations that can be suitable for use include, but are not limited to, personal computers, server computers, hand-held or laptop devices, multiprocessor systems, microprocessor-based systems, programmable consumer electronics such as smart phones, network PCs, minicomputers, mainframe computers, tablets, distributed computing environments that include any of the above systems or devices, and the like.

In its most basic configuration, operating environment 940 typically includes at least one processing unit 942 and memory 944. Depending on the exact configuration and type of computing device, memory 944 (storing, among other things, instructions to perform the display setting and control methods disclosed herein) can be volatile (such as RAM), non-volatile (such as ROM, flash memory, etc.), or some combination of the two. This most basic configuration is illustrated in FIG. 10A by dashed line 946. Further, environment 940 can also include storage devices (removable, 948, and/or non-removable, 951) including, but not limited to, solid-state devices, magnetic or optical disks, or tape. Similarly, environment 940 can also have input device(s) 954 such as touch screens, keyboard, mouse, pen, voice input, etc., and/or output device(s) 956 such as a display, speakers, printer, etc. Also included in the environment can be one or more communication connections 952, such as LAN, WAN, point to point, Bluetooth, RF, etc.

Operating environment 940 typically includes at least some form of computer readable media. Computer readable media can be any available media that can be accessed by processing unit 942 or other devices having the operating environment. By way of example, and not limitation, computer readable media can include computer storage media and communication media. Computer storage media includes volatile and nonvolatile, removable and non-removable media implemented in any method or technology for storage of information such as computer readable instructions, data structures, program modules or other data. Computer storage media includes, RAM, ROM, EEPROM, flash memory or other memory technology, CD-ROM, digital versatile disks (DVD) or other optical storage, magnetic cassettes, magnetic tape, magnetic disk storage or other magnetic storage devices, solid state storage, or any other tangible and non-transitory medium which can be used to store the desired information.

Communication media embodies computer readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above should also be included within the scope of computer readable media.

The operating environment 940 can be a single computer operating in a networked environment using logical connections to one or more remote computers. The remote computer can be a personal computer, a server, a router, a network PC, a peer device or other common network node, and typically includes many or all of the elements described above as well as others not so mentioned. The logical connections can include any method supported by available communications media. Such networking environments are commonplace in hospitals, offices, enterprise-wide computer networks, intranets and the Internet.

In some examples, the components described herein include such modules or instructions executable by computer system 940 that can be stored on computer storage medium and other tangible mediums and transmitted in communication media. Computer storage media includes volatile and non-volatile, removable and non-removable media implemented in any method or technology for storage of information such as computer readable instructions, data structures, program modules, or other data. Combinations of any of the above should also be included within the scope of readable media. In some examples, computer system 940 is part of a network that stores data in remote storage media for use by the computer system 940.

Figure 10B:
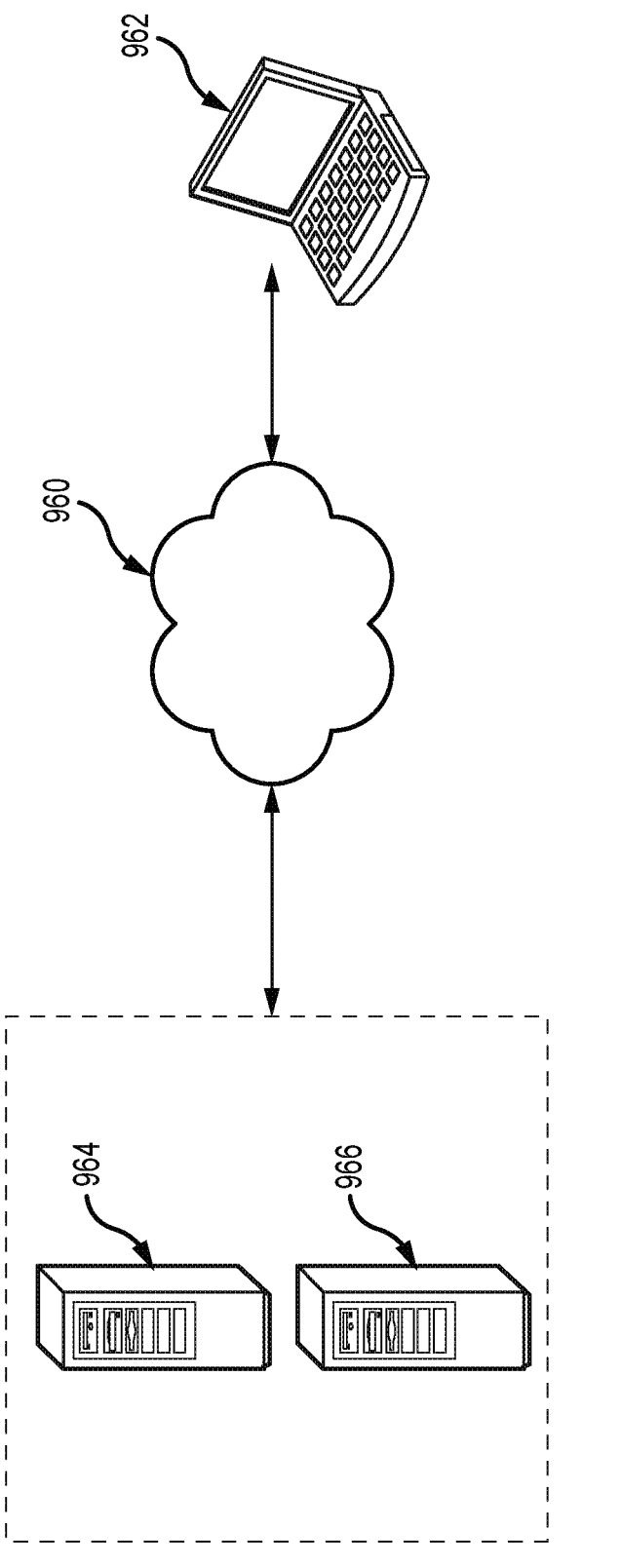
FIG. 10B depicts an example of a network in which the various systems and methods disclosed herein may operate.

FIG. 10B depicts an example of a network in which the various systems and methods disclosed herein may operate. In examples, a client device, such as client device 962, may communicate with one or more servers, such as servers 964 and 966, via a network 968. In examples, a client device may be a laptop, a personal computer, a smart phone, a PDA, a netbook, or any other type of computing device, such as the computing device in FIG. 10A. In examples, servers 964 and 966 may be any type of computing device, such as the computing device illustrated in FIG. 10A. Network 968 may be any type of network capable of facilitating communications between the client device and one or more servers 964 and 966. Examples of such networks include, but are not limited to, LANs, WANs, cellular networks, and/or the Internet.

In examples, processing of data and performance of the methods described herein may be accomplished with the use of one or more server devices. For example, in one example, a single server, such as server 964 may be employed to assist in processing data and performing the methods disclosed herein. Client device 962 may interact with server 964 via network 968. In further examples, the client device 962 may also perform functionality disclosed herein, such as scanning and processing data, which can then be provided to servers 964 and/or 966.

In alternate examples, the methods disclosed herein may be performed using a distributed computing network, or a cloud network. In such examples, the methods disclosed herein may be performed by two or more servers, such as servers 964 and 966. Although a particular network example is disclosed herein, one of skill in the art will appreciate that the systems and methods disclosed herein may be performed using other types of networks and/or network configurations. Further, the data sent to the servers and received from the servers may be encrypted. The data may also be stored in an encrypted manner both locally and on the servers.

This disclosure described some examples of the present technology with reference to the accompanying drawings, in which only some of the possible examples were shown. Other aspects can, however, be embodied in many different forms and should not be construed as limited to the examples set forth herein. Rather, these examples were provided so that this disclosure was thorough and complete and fully conveyed the scope of the possible examples to those skilled in the art.

Although specific examples were described herein, the scope of the technology is not limited to those specific examples. One skilled in the art will recognize other examples or improvements that are within the scope of the present technology. Therefore, the specific structure, acts, or media are disclosed only as illustrative examples. Examples according to the technology may also combine elements or components of those that are disclosed in general but not expressly exemplified in combination, unless otherwise stated herein. The scope of the technology is defined by the following claims and any equivalents therein.

The invention claimed is:

1. A method of setting a display orientation for a display of an imaging system, the method comprising:
    sending a default display signal to one or more displays of the imaging system, wherein the one or more displays include a compression arm display disposed on a compression arm of the imaging system or a foot display disposed on a floor mount of the imaging system, wherein the default display signal is a read-ready orientation of the one or more displays;
    determining at least one condition associated with the imaging system; and
    based on the determined condition, sending a change display signal to the one or more displays of the imaging system, wherein the change display signal changes the read-ready orientation of the one or more displays.

2. The method of claim 1, wherein the at least one condition includes a C-arm assembly of the imaging system being in a craniocaudal (CC) imaging orientation, a left mediolateral oblique (MLO) imaging orientation, or a right MLO imaging orientation.

3. The method of claim 1, wherein the at least one condition includes left interface use or right interface use of the imaging system by a technologist.

4. The method of claim 3, wherein left or right interface use includes operation of a support arm interface, operation of a gantry interface, or operation of a compression arm knob by the technologist.

5. The method of claim 1, wherein the one or more displays include the compression arm display having two compression arm displays, and a default read-ready orientation includes a footer edge of each of the two compression arm displays facing away from each other, and wherein the change display signal changes the read-ready orientation of the one or more displays to the footer edge of each of the two compression arm displays facing the same direction.

6. The method of claim 5, wherein the change display signal is only sent to one of the two compression arm displays.

7. The method of claim 1, wherein the one or more displays include the foot display having a single foot display, and a default read-ready orientation includes a footer edge of the single foot display being in a landscape position, and wherein the change display signal changes the read-ready orientation of the one or more displays to the footer edge of the single foot display being in a portrait position.

8. The method of claim 1, wherein determining the at least one condition is based on comparing the at least one condition of the imaging system to a predetermined threshold.

9. The method of claim 1, wherein the imaging system includes a sensor, and wherein determining the at least one condition includes receiving a signal from the sensor.

10. The method of claim 9, wherein the signal from the sensor includes a position signal of at least one component of the imaging system, a proximity signal of a technologist relative to the imaging system, or an input signal of an input command within the imaging system.

11. An imaging system comprising:
    a gantry extending from a floor mount;
    a C-arm assembly supported on the gantry and having a compression arm, the C-arm assembly selectively positionable in a plurality of rotated positions relative to the gantry;
    one or more displays including a compression arm display disposed on the compression arm or a foot display disposed on the floor mount;
    at least one processor; and
    memory storing instructions that, when executed by the at least one processor, cause the imaging system to perform a set of operations comprising:
        send a default display signal to the one or more displays, wherein the default display signal is a read-ready orientation of the one or more displays;
        determine at least one condition associated with the imaging system; and
        based on the determined condition, send a change display signal to the one or more displays, wherein the change display signal changes the read-ready orientation of the one or more displays.

12. The imaging system of claim 11, wherein the plurality of rotated positions of the C-arm assembly includes a craniocaudal (CC) imaging orientation, a left mediolateral oblique (MLO) imaging orientation, or a right MLO imaging orientation, and wherein the at least one condition includes the plurality of rotated positions of the C-arm assembly.

13. The imaging system of claim 11, wherein the C-arm assembly includes at least one support arm interface, the gantry includes at least one gantry interface, and the compression arm includes at least one compression arm knob, and wherein the at least one condition includes operation of one or more of the at least one support arm interface, the at least one gantry interface, or the at least one compression arm knob by a technologist.

14. The imaging system of claim 11, wherein the compression arm display has two compression arm displays, and a default read-ready orientation includes a footer edge of each of the two compression arm displays facing away from each other, and wherein the change display signal changes the read-ready orientation of the one or more displays to the footer edge of each of the two compression arm displays facing the same direction.

15. The imaging system of claim 14, wherein within the set of operations, the change display signal is only sent to one of the two compression arm displays.

16. The imaging system of claim 14, wherein the two compression arm displays are disposed on an upper surface of the compression arm.

17. The imaging system of claim 11, wherein the foot display has a single foot display, and a default read-ready orientation includes a footer edge of the single foot display being in a landscape position, and wherein the change display signal changes the read-ready orientation of the one or more displays to the footer edge of the single foot display being in a portrait position.

18. The imaging system of claim 11, wherein within the set of operations, the determination of the at least one condition is based on the at least one condition being compared to a predetermined threshold.

19. The imaging system of claim 11, wherein the imaging system includes a sensor, and wherein within the set of operations, the determination of the at least one condition includes receiving a signal from the sensor.

20. The imaging system of claim 19, wherein within the set of operations, the signal from the sensor includes a position signal of at least one component of the imaging system, a proximity signal of a technologist relative to the imaging system, or an input signal of an input command within the imaging system.

* * * * *